(12) United States Patent
Wada et al.

(10) Patent No.: US 6,673,639 B2
(45) Date of Patent: Jan. 6, 2004

(54) METHOD AND SYSTEM FOR EVALUATING POLYSILICON, AND METHOD AND SYSTEM FOR FABRICATING THIN FILM TRANSISTOR

(75) Inventors: Hiroyuki Wada, Kanagawa (JP); Nobuhiko Umezu, Kanagawa (JP); Koichi Tatsuki, Kanagawa (JP)

(73) Assignee: Sony Corporation, Tokyo (JP)

( * ) Notice: Subject to any disclaimer, the term of this patent is extended or adjusted under 35 U.S.C. 154(b) by 81 days.

(21) Appl. No.: 10/072,997

(22) Filed: Feb. 12, 2002

(65) Prior Publication Data

US 2002/0160586 A1 Oct. 31, 2002

(30) Foreign Application Priority Data

Feb. 15, 2001 (JP) .................................... 2001-039101
Apr. 12, 2001 (JP) .................................... 2001-114411

(51) Int. Cl.⁷ ............................................... H01L 21/66
(52) U.S. Cl. .............................. 438/14; 438/16; 427/8; 356/30
(58) Field of Search ............................... 438/166, 487, 438/16, 14; 427/8; 356/30

(56) References Cited

U.S. PATENT DOCUMENTS

| | | | | |
|---|---|---|---|---|
| 4,332,833 A | * | 6/1982 | Aspnes et al. ................. | 427/8 |
| 5,182,647 A | * | 1/1993 | Chang ................... | 358/213.11 |
| 5,314,831 A | * | 5/1994 | Hirae et al. | |
| 5,450,205 A | * | 9/1995 | Sawin et al. ................. | 356/382 |
| RE36,371 E | * | 11/1999 | Imahashi et al. .............. | 427/8 |
| 6,080,236 A | * | 6/2000 | McCulloch et al. ........... | 117/4 |
| 6,177,127 B1 | * | 1/2001 | Weimer et al. ................ | 427/8 |
| 6,218,198 B1 | * | 4/2001 | Imao et al. ..................... | 438/7 |
| 6,284,552 B1 | * | 9/2001 | Yamagata et al. ............ | 438/14 |
| 6,336,969 B1 | * | 1/2002 | Yamaguchi et al. ........... | 117/7 |
| 6,489,992 B2 | * | 12/2002 | Savoye ........................ | 348/340 |
| 6,555,423 B2 | * | 4/2003 | Wada et al. ................. | 438/166 |

* cited by examiner

*Primary Examiner*—Mary Wilczewski
(74) *Attorney, Agent, or Firm*—Oblon, Spivak, McClelland, Maier & Neustadt, P.C.

(57) ABSTRACT

A method of evaluating a state of a polysilicon film objectively, accurately, automatically, and in a non-contact manner is provided. The method includes the steps of picking up a surface of a polysilicon film formed by excimer laser annealing, dividing the picked-up image into meshes each having a specific size, calculating a contrast in each of the meshes, extracting a highest contrast value and a lowest contrast value in the picked-up image, calculating a contrast ratio therebetween, and judging an average grain size of the polysilicon film on the basis of the contrast ratio.

24 Claims, 19 Drawing Sheets

MIDDLE GRAIN
SIZE
250nm~450nm

↕X

INTERMEDIATE
GRAIN SIZE
450nm~800nm

↕X

LARGE GRAIN
SIZE
800nm~

↕X

MICRO GRAIN
SIZE
~10nm

↕X

METHOD AND SYSTEM FOR EVALUATING POLYSILICON, AND METHOD AND SYSTEM FOR FABRICATING THIN FILM TRANSISTOR

BACKGROUND OF THE INVENTION

The present invention relates to a polysilicon evaluating method of evaluating states of crystals of a polysilicon film and a polysilicon film evaluating system used therefore, and a thin film transistor fabricating method of fabricating a thin film transistor having a polysilicon film formed by annealing amorphous silicon and a thin film transistor fabricating system used therefore.

In recent years, thin film transistors using polysilicon films as channel layers have come to be put into practical use. A thin film transistor using a polysilicon film as a channel layer exhibits a very high field mobility, and accordingly, if being used as a drive circuit for a liquid crystal display or the like, such a thin film transistor can realize higher definition, higher operational speed, and miniaturization of the display.

On the other hand, in recent years, a so-called low temperature polycrystallization process has been developed. In this process, a polysilicon film is formed by heat-treating amorphous silicon by using an excimer laser annealing system. In the case of applying such a low temperature polycrystallization process to fabrication of thin film transistors, since a thermal damage to a substrate becomes low, it is possible to use an inexpensive glass substrate having a large area.

However, since an output power of an excimer laser annealing system used for the low temperature polycrystallization process is unstable, grain sizes of polysilicon formed by laser annealing largely vary depending on the unstable output power. As a result, grain sizes of crystals of a polysilicon film formed by using the excimer laser annealing system is not necessarily desirable. For example, if crystals of the polysilicon film thus formed have micro grain sizes, there arises a problem associated with a so-called linear failure, and if crystals of the polysilicon film have grain sizes not sufficiently large, there arises a problem associated with a so-called writing failure.

Accordingly, in the case of forming polysilicon films for a number of devices by annealing using such an excimer laser annealing system, after the end of the polycrystallization step for the polysilicon films, the devices on which the polysilicon films have been formed are generally subjected to total inspection or random sample inspection in terms of states of crystals of the polysilicon film formed on the outermost surface of each of all the devices or the randomly sampled devices, and at that stage, it is decided whether or not the devices thus semi-finished are defective, and information on an energy of a laser beam given from the excimer laser annealing system to amorphous silicon from which the polysilicon film is formed is fed back to the excimer laser annealing system, to set a laser power to an optimum value.

However, as a method of evaluating a polysilicon film, there is known only a sensible method of picking up a surface image by using a spectral ellipsometer, a scanning electron microscope or the like and judging states of crystals of the polysilicon film by visually observing the surface image thereof. Such a method fails to objectively judge states of crystals of a polysilicon film in a non-contact manner, and is not efficient in terms of time and cost. As a result, the method is difficult to be used for evaluation of the polysilicon film in-process.

SUMMARY OF THE INVENTION

An object of the present invention is to evaluate a state of a polysilicon film objectively, accurately, automatically, and in a non-contact manner.

To achieve the above object, according to a first aspect of the present invention, there is provided a polysilicon evaluating method of evaluating a polysilicon film formed by annealing an amorphous silicon film, including the steps of: picking up an image of a surface of the polysilicon film; dividing the picked-up image into a plurality of regions and calculating a contrast in each of the regions divided from the picked-up image; detecting a high contrast region and a low contrast region and comparing the contrasts in the high contrast and low contrast regions with each other; and evaluating a state of the polysilicon film on the basis of the comparison result.

According to a second aspect of the present invention, there is provided a polysilicon evaluating system for evaluating a polysilicon film formed by annealing an amorphous silicon film, including: pick-up means of picking up a surface of the polysilicon film; and evaluation means of dividing the picked-up image into a plurality of regions, calculating a contrast in each of the regions divided from the picked-up image, detecting a high contrast region and a low contrast region, comparing the contrasts in the high contrast and low contrast regions with each other, and evaluating the state of the polysilicon film on the basis of the comparison result.

According to a third aspect of the present invention, there is provided a thin film transistor fabricating method of fabricating a thin film transistor, including: amorphous silicon forming step of forming an amorphous silicon film; polysilicon film forming step of forming a polysilicon film by annealing the amorphous silicon film; and evaluating step of picking up an image of a surface of the polysilicon film, dividing the picked-up image into a plurality of regions, calculating a contrast in each of the regions divided from the picked-up image, detecting a high contrast region and a low contrast region, comparing the contrasts in the high contrast and low contrast regions, and evaluating the state of the polysilicon film on the basis of the comparison result.

According to a fourth aspect of the present invention, there is provided a thin film transistor fabricating system for fabricating a thin film transistor, including: an amorphous silicon forming device for forming an amorphous silicon film; a polysilicon film forming device for forming a polysilicon film by annealing the amorphous silicon film; and an evaluating device for picking up an image of a surface of the polysilicon film, dividing the picked-up image into a plurality of regions, calculating a contrast in each of the regions divided from the picked-up image, detecting a high contrast region and a low contrast region, comparing the contrasts in the high contrast and low contrast regions, and evaluating the state of the polysilicon film on the basis of the comparison result.

According to the polysilicon evaluating method and the polysilicon evaluating system of the present invention, it is possible to evaluate a state of a polysilicon film objectively, accurately, automatically, and in a non-contact manner.

According to the thin film transistor fabricating method and the thin film transistor fabricating system, it is possible to easily inspect a polysilicon film in a nondestructive manner, and hence to incorporate the inspection step in the fabrication process. Also, since the inspection can be performed on the basis of numerical calculation without the need of visual inspection, it is possible to automate the inspection and to objectively perform the inspection at a high accuracy. Further, it is possible to enhance a fabrication yield of thin film transistors by feeding back am inspection result to an annealing step.

DETAILED DESCRIPTION OF THE PREFERRED EMBODIMENTS

Figure 1:
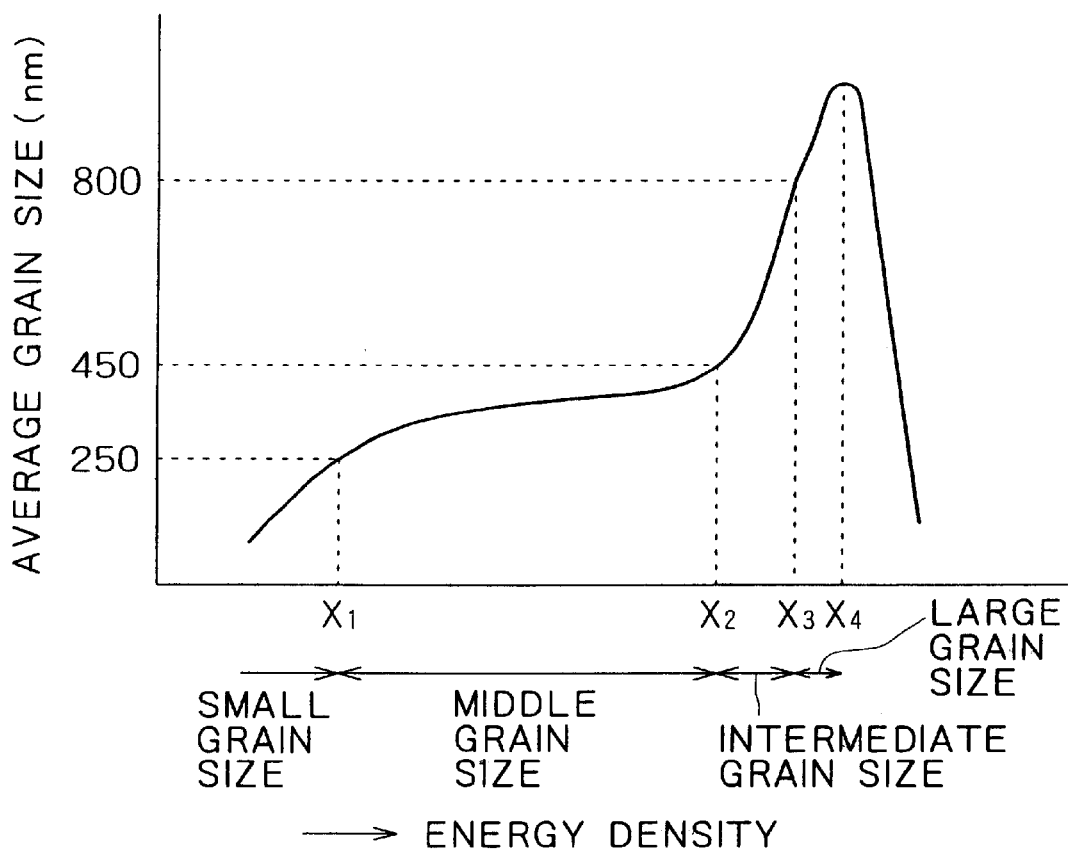
FIG. 1 is a graph illustrating a relationship between grain sizes of crystals of a polysilicon film and an energy given to an amorphous silicon film at the time of excimer laser annealing for forming the polysilicon film by polycrystallizing the amorphous silicon film.

Hereinafter, preferred embodiments of a polysilicon film evaluating system and a polysilicon film evaluating method, and a thin film fabricating system using the polysilicon film evaluating system and a thin film fabricating method using the polysilicon film evaluating method according to the present invention will be described with reference to the drawings.

A polysilicon film evaluating system according to an embodiment of the present invention is typically used for inspecting a polysilicon film formed in a process of fabricating a thin film transistor having a top-gate structure (hereinafter, referred to as "top-gate type TFT"). The top-gate type TFT is configured such that a polysilicon film (channel layer), a gate insulating film, and a gate electrode are stacked, for example, on a glass substrate in this order from the substrate side. In other words, in the top-gate type TET, the polysilicon film functioning as a channel layer is formed at the lowermost layer on the substrate side.

A polysilicon film of the top-gate type TFT is formed by depositing amorphous silicon (a-Si) by an LPCVD process or the like, and polycrystallizing the amorphous silicon by annealing. In the step of forming a polysilicon film by polycrystallizing amorphous silicon, the amorphous silicon is polycrystallized by laser annealing using an excimer laser beam representative of an ultraviolet laser beam. The excimer laser annealing is performed by irradiating a linear region of an amorphous silicon film with a linear-shaped pulse laser beam and moving the linear region of the amorphous silicon film irradiated with the pulse laser beam, to polycrystallize the amorphous silicon film, thereby forming a polysilicon film. In this laser beam annealing, a shape of the linear region irradiated with the laser beam is typically set to a shape having a length of 20 cm in the longitudinal direction (long-side direction) and a length of 400 μm in the width direction (short-side direction); a frequency of the pulse of the laser beam is typically set to 300 Hz; and a scanning direction of the laser beam is set to a direction perpendicular to the longitudinal direction, that is, to the short-side direction of the region irradiated with the linear laser beam.

In the top-gate type TFT configured as described above, since a channel layer is made from polysilicon, a field mobility of the channel layer is very high. As a result, in the case of using such a top-gate TFT as a drive circuit of a liquid crystal display or the like, it is possible to realize higher definition, higher operating speed, miniaturization, and the like of the display. Further, in a process of fabricating the top-gate type TFT, since a polysilicon film is formed by a so-called low temperature polycrystallization process in which heat-treatment of amorphous silicon is performed by using excimer laser annealing, it is possible to reduce a thermal damage to a substrate in the polycrystallization process, and to use an inexpensive glass plate having a large area as the substrate.

It is known that an important factor of determining a field mobility of a polysilicon film is grain sizes of polysilicon. Grain sizes of polysilicon is largely dependent on an energy of a laser beam given to amorphous silicon at the time of excimer laser annealing for forming a polysilicon film by polycrystallizing the amorphous silicon. Accordingly, control and stabilization of an energy density of a laser beam at the time of excimer laser annealing exert a large effect on characteristics and a production yield of each finished top-gate TFT using the polysilicon film.

An excimer laser annealing system used for excimer laser annealing, however, has an inconvenience that a variation in output of an energy of a laser beam emitted from the system is relatively large. As a result, when an amorphous silicon film is polycrystallized by excimer laser annealing using the excimer laser annealing system to form a polysilicon film, an energy given to the amorphous silicon film is liable to be largely deviated from an allowable range of an energy, which range is determined so as to be able to form a suitable polysilicon film composed of crystals having desirable grain sizes, and which range means a production margin of a suitable polysilicon film, so that it is difficult to stably produce a suitable polysilicon film.

Accordingly, in the case of forming a plurality of polysilicon films by excimer laser annealing under the same condition, grain sizes of crystals for one polysilicon silicon may be different from that of another polysilicon film. For example, if a laser energy becomes excessively large, then amorphous silicon is polycrystallized into microcrystals of silicon, while if the laser energy becomes excessively small, then amorphous silicon is polycrystallized into crystals of silicon having small grain sizes, that is, cannot be polycrystallized into crystals of silicon having large grain sizes sufficiently.

Accordingly, in the case of forming polysilicon films for a number of devices by annealing using such an excimer laser annealing system, after the end of the polycrystallization step for the polysilicon films, the devices on which the polysilicon films have been formed are generally subjected to total inspection or random sample inspection in terms of states of crystals of the polysilicon film formed on the outermost surface of each of all the devices or the randomly sampled devices, and at that stage, it is decided whether or not the devices thus semi-finished are defective, and also information obtained by evaluating crystal states of each polysilicon film and calculating energy density of a laser beam given from the excimer laser annealing system to amorphous silicon from which the polysilicon film is formed is fed back to the excimer laser annealing system, to adjust the energy density of a laser beam emitted therefrom.

A polysilicon film evaluating system is typically used to evaluate a polysilicon film formed by polycrystallization after the end of the polycrystallization step, and to decide whether or not the semi-finished product on which the polysilicon film has been formed is defective at that stage, or to feed back the evaluation information to the excimer laser annealing system for adjusting energy density of a laser beam emitted therefrom.

The principle of evaluating a polysilicon film formed by the above-described excimer laser annealing will be described below.

Grain sizes of crystals of a polysilicon film are largely dependent on an energy given by excimer laser annealing. Referring to FIG. 1, as a given energy is increased, grain sizes of a polysilicon film are correspondingly increased; however, when the energy is increased to an energy point $X_1$ or more, the grain sizes are grown to somewhat large sizes, and thereafter, are not increased so much, that is, stabilized. An average particle size of crystals of the polysilicon film at that time is typically 250 nm. When the energy is further increased to an energy point $X_2$ or more, the grain sizes start to be largely increased again. An average particle size of crystals of the polysilicon film at that time is typically 450 nm. When the energy reaches an energy point $X_3$ (immediately before a critical energy point $X_4$), grain sizes become sufficiently large. An average particle size of crystals of the polysilicon film is typically 800 nm or more. When the energy becomes a value more than the critical energy point $X_4$, grain sizes become significantly fine. At that time, crystals of the polysilicon film become microcrystals.

According to the present invention, grain sizes whose average value is less than 250 nm are called "small grain sizes"; grain sizes whose average value is 250 nm or more and less than 450 nm are called to "middle grain sizes"; grain sizes whose average value is 450 nm or more and less than 800 nm are called "intermediate grain sizes"; grain sizes whose average value is 800 nm or more are called "large grain sizes"; and grain sizes whose average value is 10 nm or less are called "micro grain sizes". It is to be noted that crystals having micro grain sizes are called "microcrystals".

A field mobility of a thin film transistor by using a polysilicon film formed as described above is largely changed depending on grain sizes of crystals of the polysilicon film. To obtain a large field mobility of a thin film transistor, grain sizes of crystals of a polysilicon film used therefor are preferably set to be large. In the case of using a polysilicon film formed by excimer laser annealing for a TFT, grain sizes of crystals of the polysilicon film may be generally either of middle grain sizes, intermediate grain sizes, and large grain sizes.

A change in image of a surface of a polysilicon film depending on a change of grain sizes of crystals of the polysilicon film caused by a change in energy density of an excimer laser beam will be described below.

Figure 2:
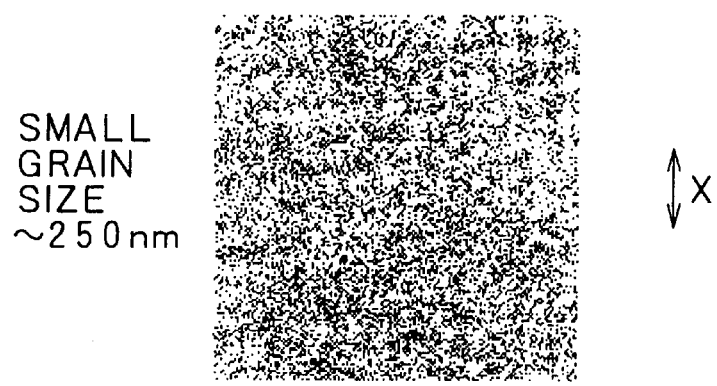
FIG. 2 is a photograph showing an image of a surface of a polysilicon film composed of crystals having small grain sizes whose average value is less than 250 nm, the image being picked-up by an ultraviolet ray microscope device.
Figure 3:
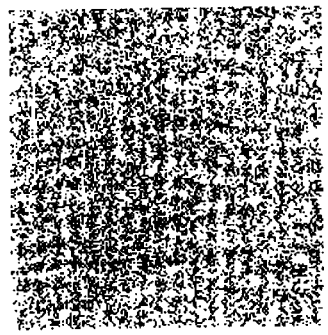
FIG. 3 is a photograph showing an image of a surface of a polysilicon film composed of crystals having middle grain sizes whose average value is 250 nm or more and less than 450 nm, the image being picked-up by the ultraviolet ray microscope device.
Figure 4:
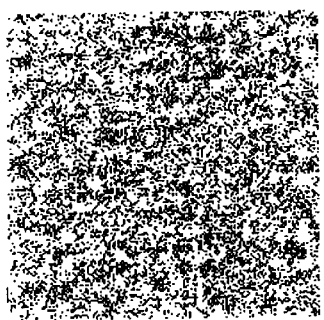
FIG. 4 is a photograph showing an image of a surface of a polysilicon film composed of crystals having intermediate grain sizes whose average value is 450 nm or more and less than 800 nm, the image being picked-up by the ultraviolet ray microscope device.
Figure 5:
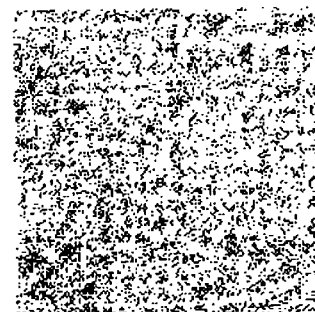
FIG. 5 is a photograph showing an image of a surface of a polysilicon film composed of crystals having large grain sizes whose average value is 800 nm or more, the image being picked-up by the ultraviolet ray microscope device.
Figure 6:
FIG. 6 is a photograph showing an image of a surface of a polysilicon film composed of microcrystals having micro grain sizes whose average value is 10 nm or less, the image being picked-up by the ultraviolet ray microscope device.

FIG. 2 shows an image of a surface of a polysilicon film composed of crystals having small grain sizes; FIG. 3 shows an image of a surface of a polysilicon film composed of crystals having middle grain sizes; FIG. 4 shows an image of a surface of a polysilicon film composed of crystals having intermediate grain sizes; FIG. 5 shows an image of a surface of a polysilicon film composed of crystals having large grain sizes; and FIG. 6 shows an image of a surface of a polysilicon film composed of microcrystals having micro grain sizes. It is to be noted that each of the images shown in FIGS. 2 to 6 is picked-up by a microscope device using an ultraviolet ray, which device will be fully described later. In FIGS. 2 to 6, a scanning direction of a laser beam used for excimer laser annealing is set to an X-direction in the figure. Each of the picked-up images shown in FIGS. 2 to 6 has an approximately square shape (size: 5.6 μm×5.6 μm), which is cut out of the polysilicon film.

Figure 7:
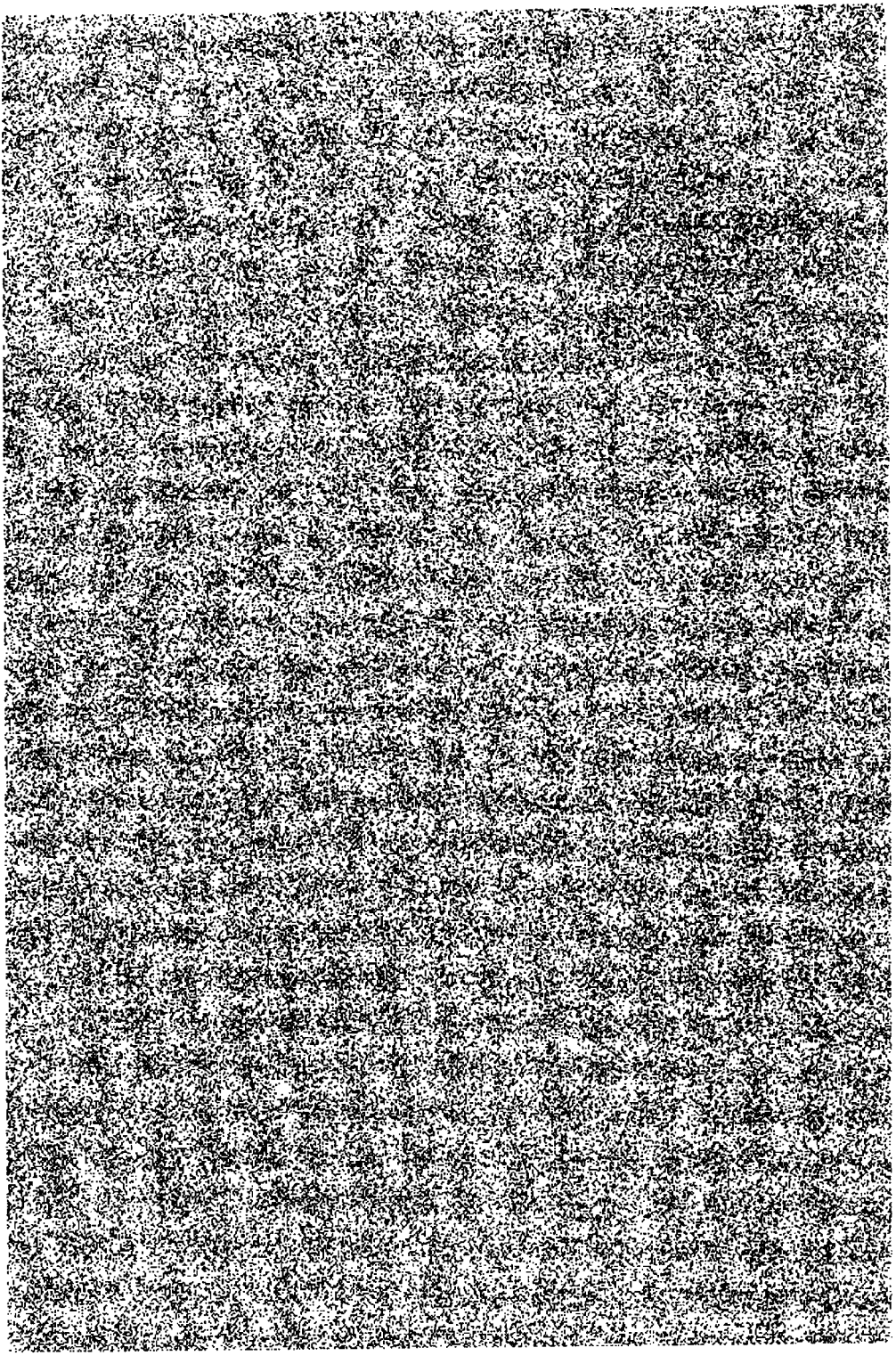
FIG. 7 is a photograph showing an enlarged image of a surface of a polysilicon film composed of crystals having small grain sizes whose average value is less than 250 nm, the image being picked-up by the ultraviolet ray microscope device.
Figure 8:
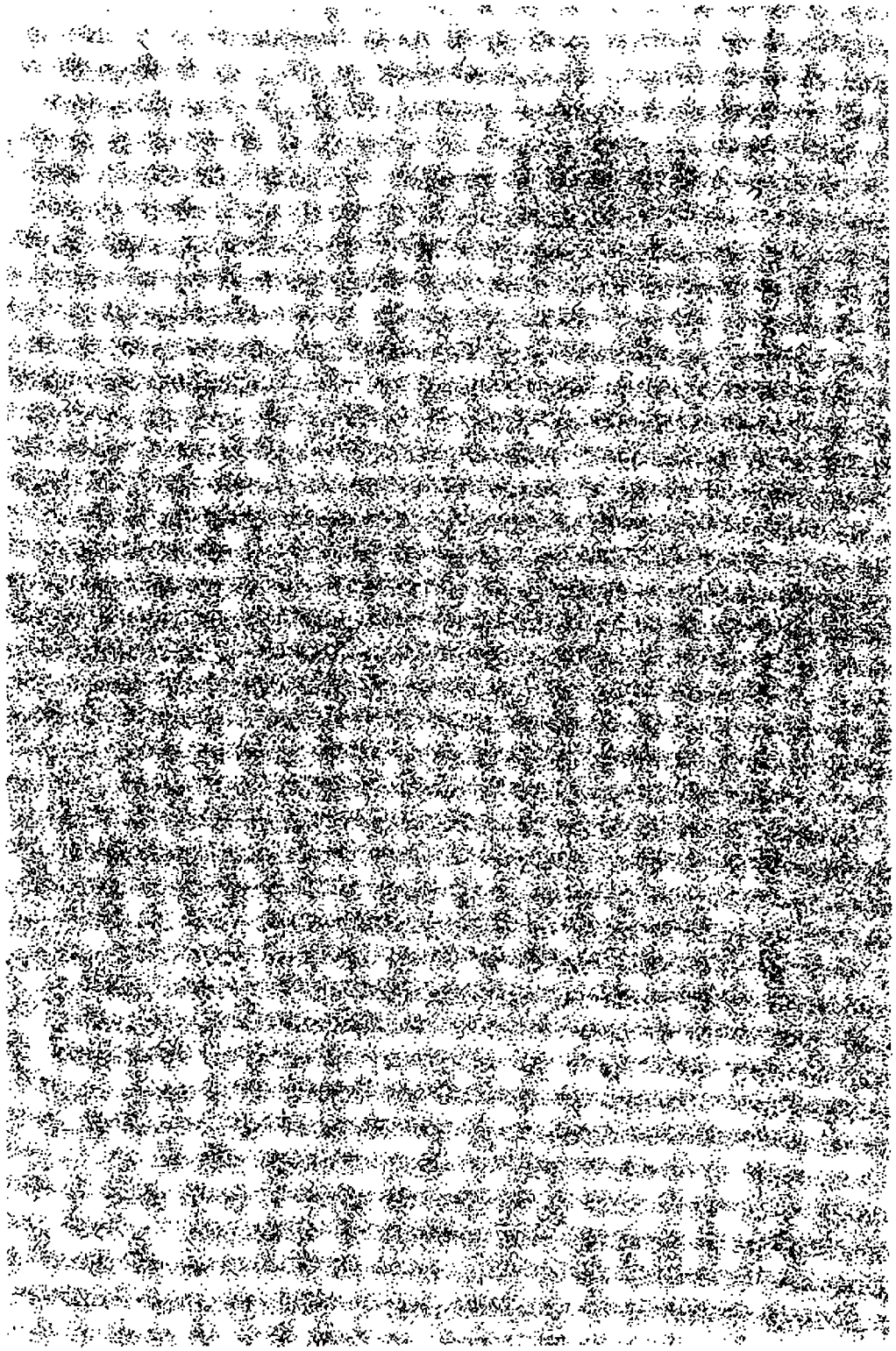
FIG. 8 is a photograph showing an enlarged image of a surface of a polysilicon film composed of crystals having middle grain sizes whose average value is 250 nm or more and less than 450 nm, the image being picked-up by the ultraviolet ray microscope device.
Figure 9:
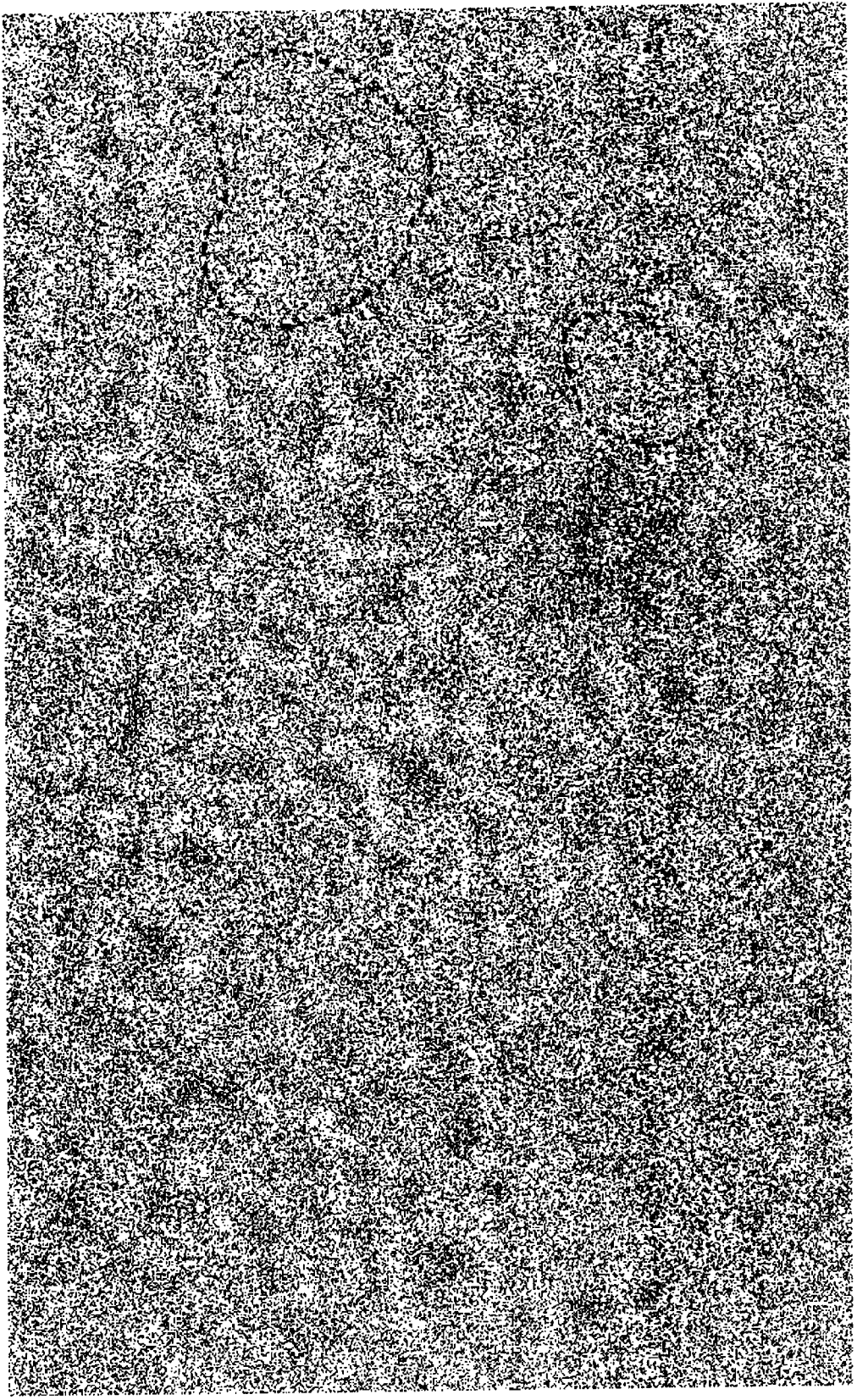
FIG. 9 is a photograph showing an enlarged image of a surface of a polysilicon film composed of crystals having large grain sizes whose average value is 800 nm or more, the image being picked-up by the ultraviolet ray microscope device.
Figure 10:
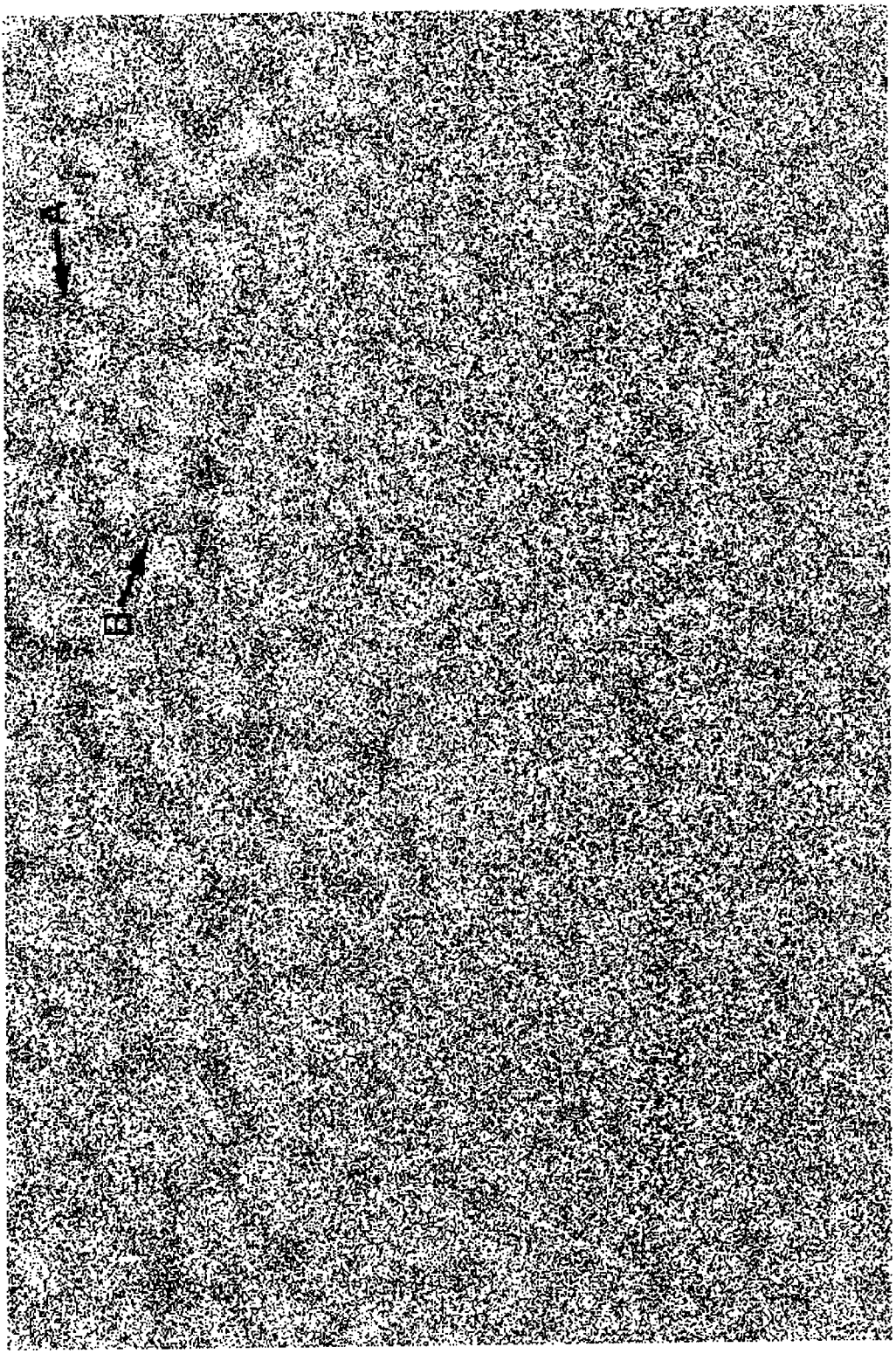
FIG. 10 is a photograph showing an enlarged image of a surface of a polysilicon film composed of microcrystals having micro grain sizes whose average value is 10 nm or less, the image being picked-up by the ultraviolet ray microscope device.

FIG. 7 shows an enlarged image of a surface of a polysilicon film composed of crystals having small grain sizes; FIG. 8 shows an enlarged image of a surface of a polysilicon film composed of crystals having middle grain sizes; FIG. 9 shows an enlarged image of a surface of a polysilicon film composed of crystals having large grain sizes; and FIG. 10 shows an enlarged image of a surface of a polysilicon film composed of microcrystals having micro grain sizes. Each of the picked-up images shown in FIGS. 7 to 10 has a rectangular shape (size: 12 μm×8 μm), which is cut out of the polysilicon film.

As a result of comparison between the picked-up images for respective grain sizes, it is revealed that the following features appear in the picked-up images for respective grain sizes.

In the case of the surface image for small grain sizes (see FIGS. 2 and 7), the image plane is uniformly whiten and thereby has a low contrast as a whole.

In the case of the surface image for middle grain sizes (see FIGS. 3 and 8), black points discretely appear in the entire image plane, and thereby the image plane has a high contrast as a whole; and the black points are arrayed linearly in the scanning direction of the laser beam at the time of laser annealing and straight lines composed of the black points periodically appear in the direction perpendicular to the scanning direction of the laser beam.

In the case of the surface image for intermediate grain sizes (see FIG. 4), like the surface image for middle grain sizes, black points discretely appear in the entire image plane and thereby the image plane has a high contrast as a whole; however, unlike the surface image for middle grain sizes, the linearity of the black points disappears.

In the case of the surface image for large grain sizes (see FIGS. 5 and 9), both a high contrast portion in which black points discretely appear and a low contrast portion (white mottle portion) appear. For example, the white mottle portion with a low contrast is shown as a region surrounded by a black frame in FIG. 9, which is a region sufficiently larger than the black point.

In the case of the surface image for micro grain sizes (see FIGS. 6 and 10), like the surface image for large grain sizes, a white mottle portion with a low contrast appears, a size of which is very larger than that of the white mottle portion appearing in the surface image for large grain sizes; and as shown by characters A and B in FIG. 10, unlike the surface images for middle grain sizes, intermediate grain sizes and large grain sizes, black points are closer or joined to each other to form continuous black lines.

In this way, the above-described various features appear in images of surfaces of polysilicon films, formed by laser annealing, composed of crystals having different grain sizes.

States of grain sizes of crystals of a polysilicon film can be thus determined by processing a picked-up image of a surface of the polysilicon film and performing judgement as described below.

It can be distinguished whether grain sizes of crystals of a polysilicon film are large grain sizes (or micro grain sizes) or the other grain sizes by judging whether or not both a high contrast portion in which black points appear and a low contrast portion (white mottle portion) appear in a picked-up image of the surface of the polysilicon film.

It can be distinguished whether grain sizes of crystals of a polysilicon film are middle grain sizes (or intermediate grain sizes or large grain sizes) or the other grain sizes by judging whether or not the entire picked-up image of a surface of the polysilicon film has a high contrast. This is because, in each of the surface images for middle grain sizes, intermediate grain sizes and large grain sizes, the image plane has a number of portions in each of which black points discretely appear, and thereby has a high contrast as a whole.

It can be distinguished whether grain sizes of crystals of a polysilicon film are small grain sizes (or micro grain sizes) or the other grain sizes by judging an area of white mottle portions with low contrasts (low contrast regions) in a picked-up image of a surface of the polysilicon film. This is because, in each of the surface images for small grain sizes and micro grain sizes, an area of low contrast regions becomes significantly large.

It can be distinguished whether grain sizes of crystals of a polysilicon film are middle grain sizes or the other grain sizes by judging whether or not linearity and periodicity appear over the entire picked-up image of a surface of the polysilicon film. This is because, in the surface image for middle grain sizes, black points are arrayed linearly in the scanning direction of an excimer laser beam, and the straight lines composed of the black points periodically appear in the direction perpendicular to the scanning direction of the excimer laser beam.

It can be distinguished whether grain sizes of crystals of a polysilicon film are micro grain sizes or the other grain sizes by judging whether or not black continuous lines are present in a picked-up image of a surface of the polysilicon film, or judging a length of each black continuous line.

FIGS. 11A to 11E show results of measuring relationships between a change in energy density of a laser beam given at the time of excimer laser annealing and changes in average grain size, contrast ratio, area of a low contrast section, length of a continuous line, and AC value, of a polysilicon film, respectively.

Figure 11A:
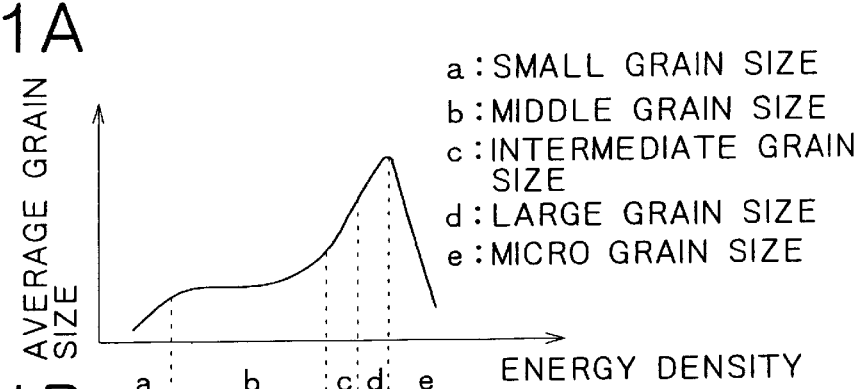
FIGS. 11A to 11E are graphs showing relationships between a change in energy density of a laser beam used for excimer laser annealing and changes in average grain size, contrast ratio, area of a low contrast region, length of a continuous line, and AC value of a polysilicon film formed by the excimer laser annealing.
Figure 11B:
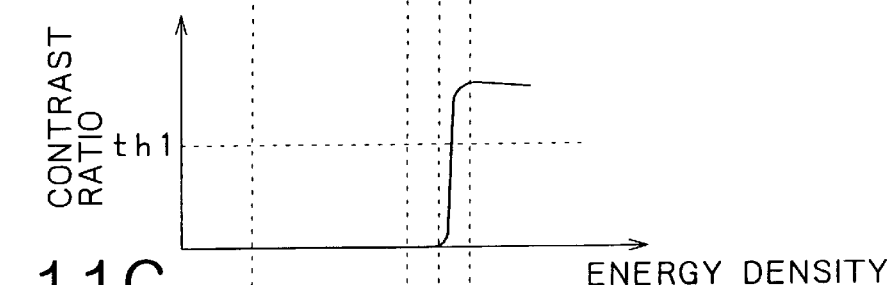

As shown in FIG. 11B, for small grain sizes, middle grain sizes or intermediate grain sizes, a contrast ratio between a maximum contrast value and a minimum contrast value is as very small as approximately zero, while for large grain sizes or micro grain sizes, the contrast ratio is high. Accordingly, it can be distinguished whether grain sizes of crystals of a polysilicon film are large grain sizes (or micro grain sizes) or the other grain sizes by calculating a contrast ratio from a picked-up image of a surface of the polysilicon film and comparing the contrast ratio with a specific threshold value (th1).

Figure 11C:
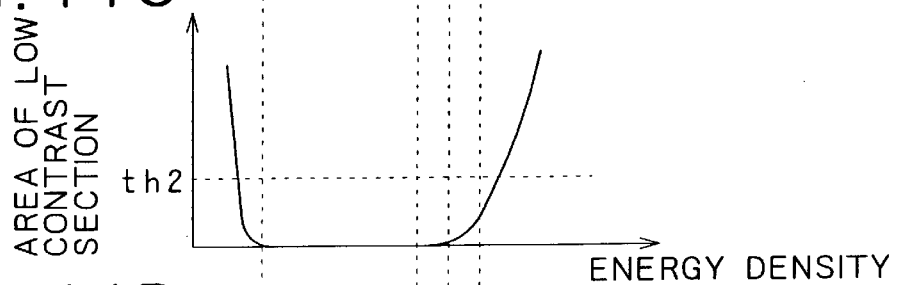

As shown in FIG. 11C, for small grain sizes or micro grain sizes, an area of a low contrast section is large, while for middle grain sizes, intermediate grain sizes or large grain sizes, the area of the low contrast section is low. Accordingly, it can be distinguished whether grain sizes of crystals of a polysilicon film are small grain sizes (or micro grain sizes) or the other grain sizes by calculating an area of a low contrast section from a picked-up image of a surface of a polysilicon film and comparing the area of the low contrast section with a specific threshold value (th2).

Figure 11D:
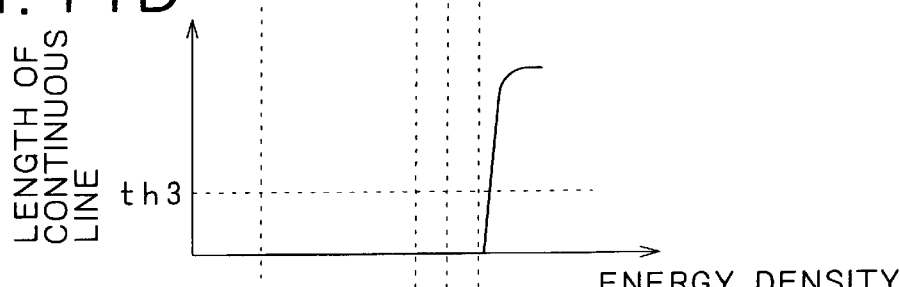

As shown in FIG. 11D, for micro grain sizes, a length of each continuous line composed of continuous black points, while for small grain sizes, middle grain sizes, intermediate grain sizes or large grain sizes, the length of each continuous line is short. That is to say, for small grain sizes, middle grain sizes, intermediate grain sizes or large grain sizes, black points are discretely dotted. Accordingly, it can be distinguished whether grain sizes of crystals of a polysilicon film are micro grain sizes or the other grain sizes by measuring a length of each continuous line from a picked-up image of a surface of the polysilicon film and comparing the length of the continuous line with a specific threshold value (th3).

Figure 11E:
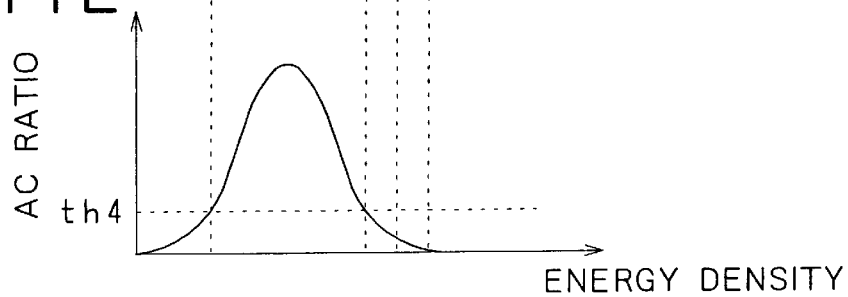

As shown in FIG. 11E, for middle grain sizes, an AC value is large, while for small grain sizes, intermediate grain sizes, large grain sizes or micro grain sizes, the AC value is small. The AC value is an abbreviation of an autocorrelation (AC) of a picked-up image. In the case where the AC value of a picked-up image is high, a periodicity of the picked-up image is large. That is to say, the AC value becomes a parameter indicating a phenomenon that black points linearly appear and the straight lines periodically appear. In addition, as described above, such a phenomenon is the feature of a picked-up image of a surface of a polysilicon film composed of crystals having middle grains. Accordingly, it can be distinguished whether grain sizes of crystals of a polysilicon film are middle grain sizes or the other grain sizes by calculating an AC value from a picked-up image of a surface of a polysilicon film and comparing the AC value with a specific threshold value (th4).

A concrete configuration example of a polysilicon film evaluating system for evaluating a polysilicon film as described above will be described below.

The polysilicon film evaluating system is used to pick up an image of a substrate for a top-gate type TFT, (which substrate is in a state immediately after a polysilicon film is formed thereon by subjecting an amorphous silicon film to excimer laser annealing) by a microscope device using an ultraviolet laser beam having a wavelength of 266 nm, and to evaluate a state of the polysilicon film from the picked-up image.

Figure 12:
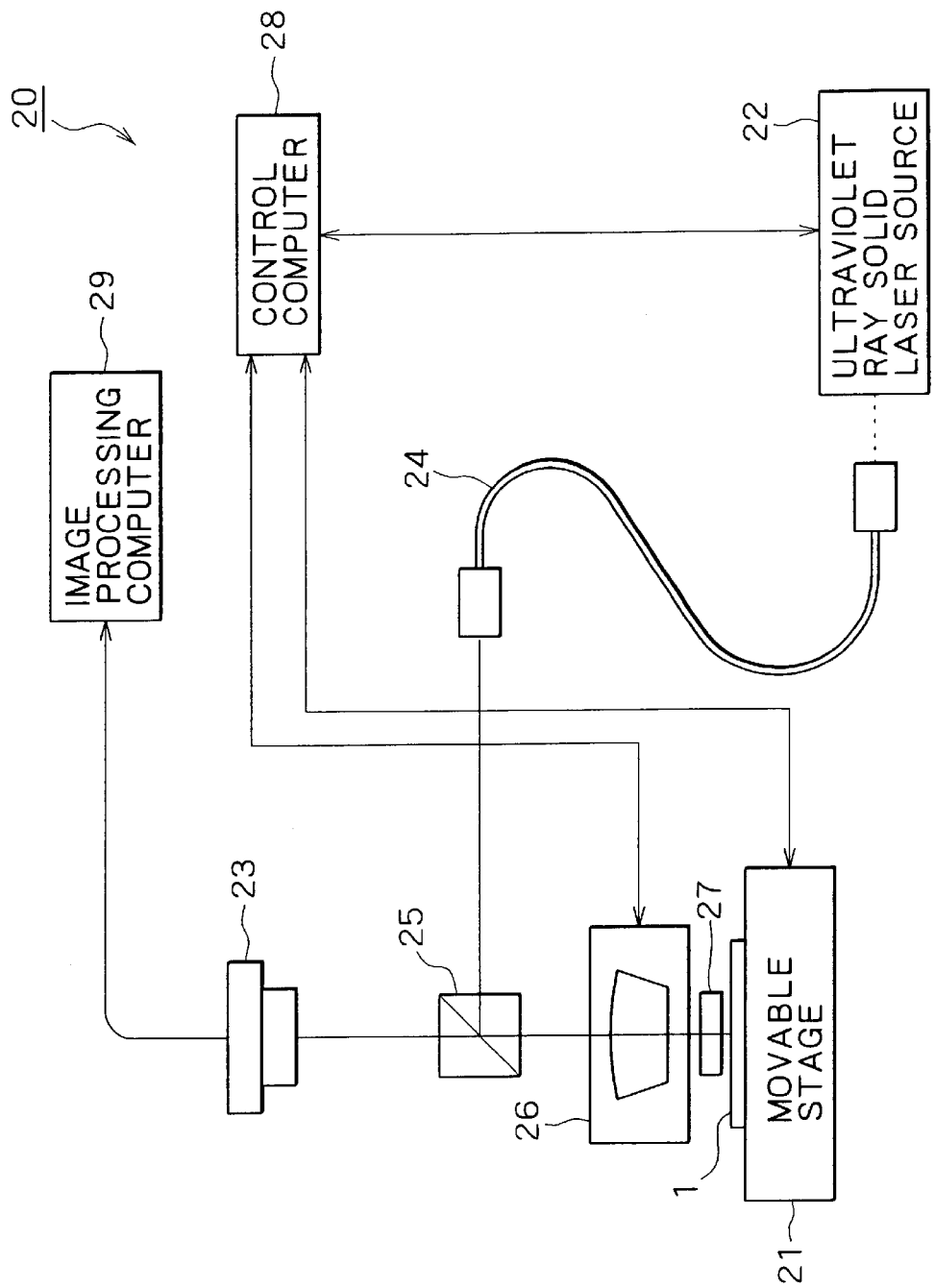
FIG. 12 is a diagram showing a configuration of a polysilicon film evaluating system.

FIG. 12 is a diagram showing a configuration of the polysilicon film evaluating system.

A polysilicon film evaluating system 20 shown in FIG. 12 includes a movable stage 21, an ultraviolet solid laser source 22, a CCD camera 23, an optical fiber probe 24, a polarization beam splitter 25, an objective lens 26, a quarter wavelength plate 27, a control computer 28, and a image processing computer 29.

The movable stage 21 is used for supporting a substrate on which a polysilicon film to be inspected has been formed. The movable stage 21 also has a function of moving the substrate to a specific position at which the substrate is to be inspected.

The movable stage 21 includes an X-stage, a Y-stage, a Z-stage, and an attracting plate.

Each of the X-stage and Y-stage is movable in the horizontal direction. A substrate to be inspected is moved in directions perpendicular to each other by the X-stage and Y-stage, to be led to a specific inspection position. The Z-stage is movable in the vertical direction for adjusting a height of a substrate. That is to say, the Z-stage is movable in an optical axis direction of an ultraviolet laser beam for irradiation of a substrate, that is, in a direction perpendicular to a plane of the substrate.

The ultraviolet solid laser source 22 emits a laser beam having a wavelength of 266 nm, and is exemplified by an Nd:YAG quadruple-wave total solid laser. In addition, recently, an ultraviolet laser source having a wavelength of about 157 nm has been developed. Such a laser source may be used.

The CCD camera 23 is a camera highly sensitive against ultraviolet rays, which internally include a CCD image sensor as an image pick-up device. A surface of a substrate is picked-up by such a CCD image sensor. A main body of the CCD camera 23 is cooled to suppress occurrence of heat noise, readout noise, circuit noise, and the like in the CCD image sensor.

The optical fiber probe 24 is a waveguide of an ultraviolet laser beam. More specifically, the optical fiber probe 24 leads an ultraviolet laser beam emitted from the ultraviolet solid laser source 22 to the polarization beam splitter 25.

The polarization beam splitter 25 reflects an ultraviolet laser beam emitted from the ultraviolet solid laser source 22. A substrate on the movable stage 21 is irradiated with the ultraviolet laser beam thus reflected through the objective lens 26. On the other hand, the polarization beam splitter 25 allows transmission of a laser beam reflected from the substrate. The laser beam, which has been reflected from the substrate and has passed through the polarization beam splitter 25, enters the high sensitivity/low noise camera 23. In this way, the polarization beam splitter 25 functions as a laser beam separator for separating an optical path of an optical system for a laser beam emitted from the ultraviolet solid laser source 22 and an optical path of an optical system for a reflected laser beam entering the CCD camera 23 from each other.

The objective lens 26 is an optical device for enlarging a laser beam reflected from a substrate. For the objective lens 26, a numerical aperture (NA) is set to 0.9, and an aberration is corrected at a wavelength of 266 nm. The objective lens 26 is disposed between the polarization beam splitter 25 and the movable stage 21.

The quarter-wave plate 27 extracts a reflected beam component from an ultraviolet laser beam. The linearly polarized ultraviolet laser beam is circularly polarized by the quarter-wave plate 27. The circularly polarized laser beam is reflected from a substrate, and is linearly polarized again by the quarter-wave plate 27. At this time, the direction of the linear polarization is rotated by 90°. Accordingly, the reflected laser beam passes through the polarization beam splitter 25.

The control computer 28 performs control of turn-on/turn-off of a laser beam emitted from the ultraviolet solid laser source 22, control of a movement position of the movable stage 21, control of changeover of the objective lens 26 and the like.

The image processing computer 29 takes in an image of a substrate, picked-up by the CCD image sensor of the CCD camera 23, and analyzes the image for evaluating a state of a polysilicon film formed on the substrate.

In the evaluating system 20 having the above-described configuration, an ultraviolet laser beam emitted from the ultraviolet solid laser source 22 enters a substrate through the optical fiber probe 24, the polarization beam splitter 25, the objective lens 26, and the quarter-wave plate 27. A linearly polarized laser beam is circularly polarized by the quarter-wave plate 27, and the circularly polarized laser beam enters the substrate. A circularly polarized laser beam reflected from the substrate is linearly polarized again by the quarter-wave plate 27. At this time, since a phase of the reflected laser beam is changed by 90°, the direction of the linear polarization is turned by 90°. Accordingly, the reflected laser beam passes through the polarization beam splitter 25 and enters the CCD camera 23. The CCD camera 23 picks up the reflected laser beam by the CCD image sensor, and surface image information of a polysilicon film thus obtained is supplied to the image processing computer 29.

The image processing computer 29 evaluates, as will be described below, a state of a polysilicon film on the basis of information of a surface image of the polysilicon film taken therein. On the basis of the evaluation result, a setting value of an energy density of a laser beam at the time of excimer laser annealing for forming the polysilicon film, and also it is decided whether a polysilicon film formed on the substrate is non-defective or defective.

According to the present invention, a surface of a polysilicon film may be evaluated not only by the ultraviolet microscope device but also by a visual light microscope device or a scanning electron microscope (SEM) device.

A first evaluation procedure for evaluating grain sizes of crystals of a polysilicon film will be described below.

Figure 13:
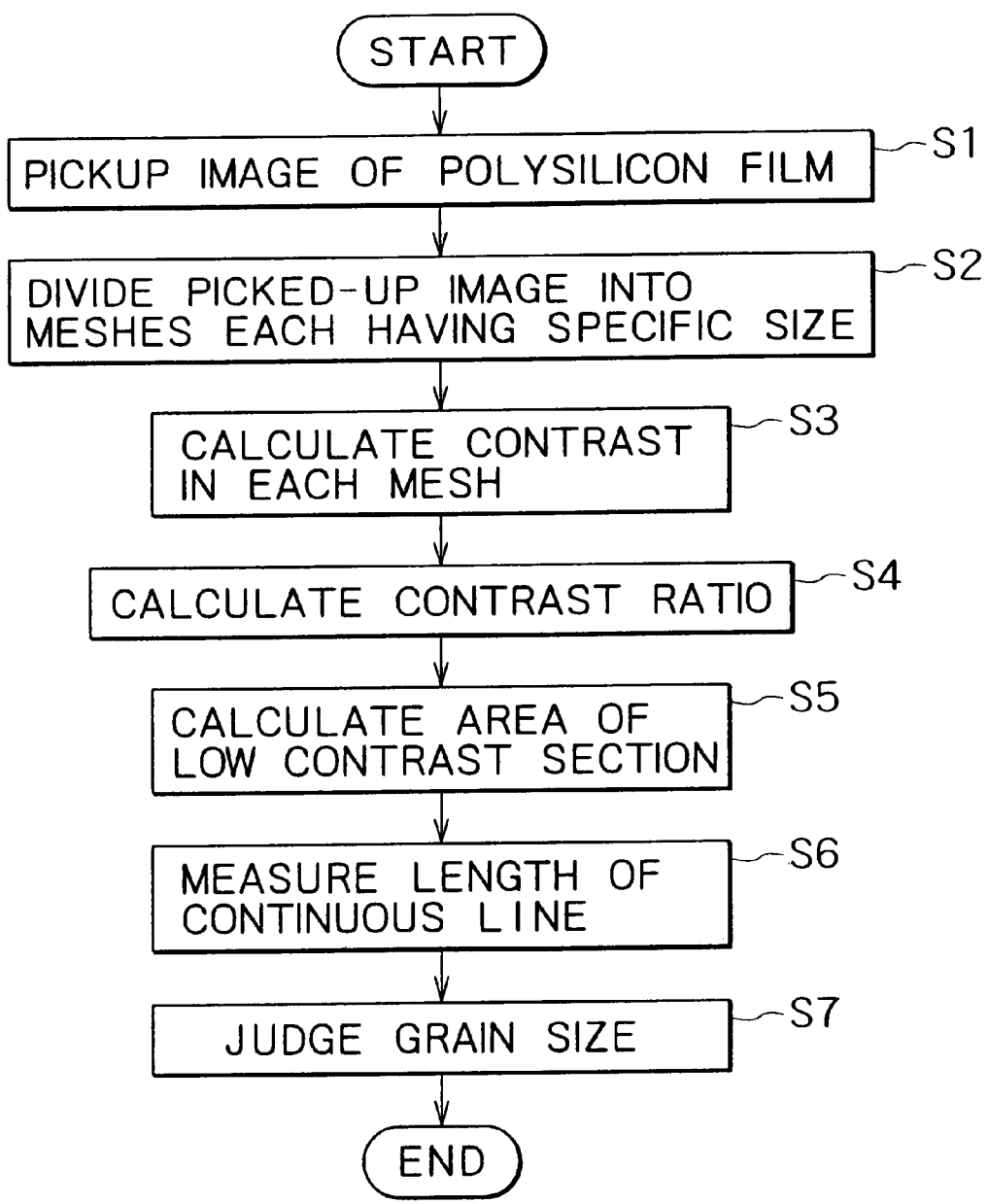
FIG. 13 is a flow chart showing a first evaluating procedure for evaluating grain sizes of crystals of a polysilicon film.

FIG. 13 shows a flow chart illustrating the first evaluation procedure.

In step S1, an image of a surface of a polysilicon film is picked-up. Such a picked-up image typically has a size of 5.6 $\mu$m square.

Figure 14:
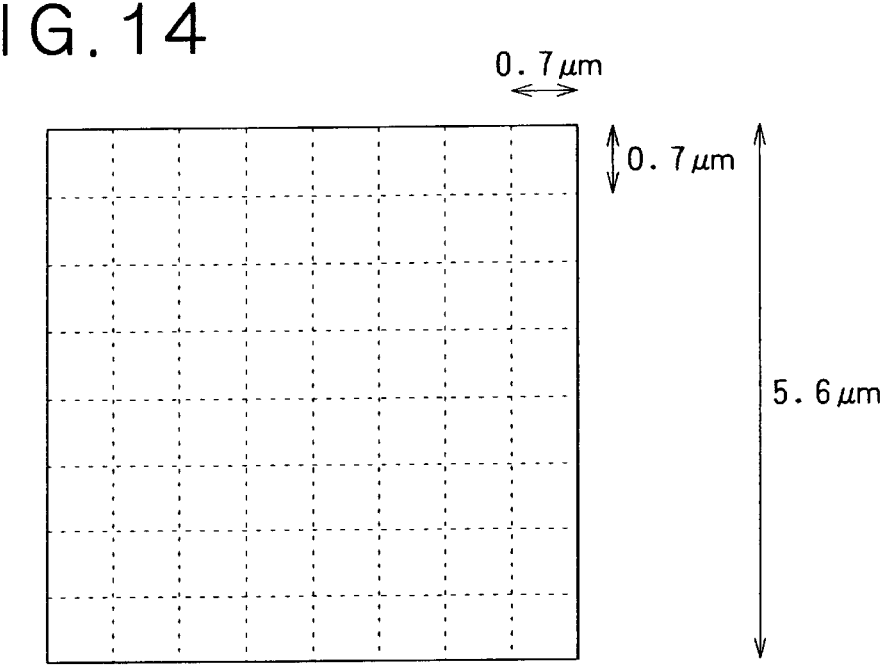
FIG. 14 is a diagram illustrating division of a picked-up image plane of a polysilicon film into meshes each having a specific size.

In step S2, as shown in FIG. 14, the entire picked-up image is divided into meshes each having a specific size of, typically, 0.7 $\mu$m square. In this case, the size of each mesh is preferably larger than that of a black point appearing for crystals having middle grain sizes, and is preferably sufficiently smaller than that of a while mottle appearing for crystals having large grain sizes.

In step S3, a contrast in each mesh is calculated by making use of a differential value of a brightness of an edge portion of the image, the degree of modulation of a brightness of each pixel, a standard deviation of respective pixels, and the like.

In step S4, a maximum contrast value and a minimum contrast value in the picked-up image are extracted from the calculated contrast values, and the contrast ratio between the maximum and minimum contrast values is calculated.

Figure 15:
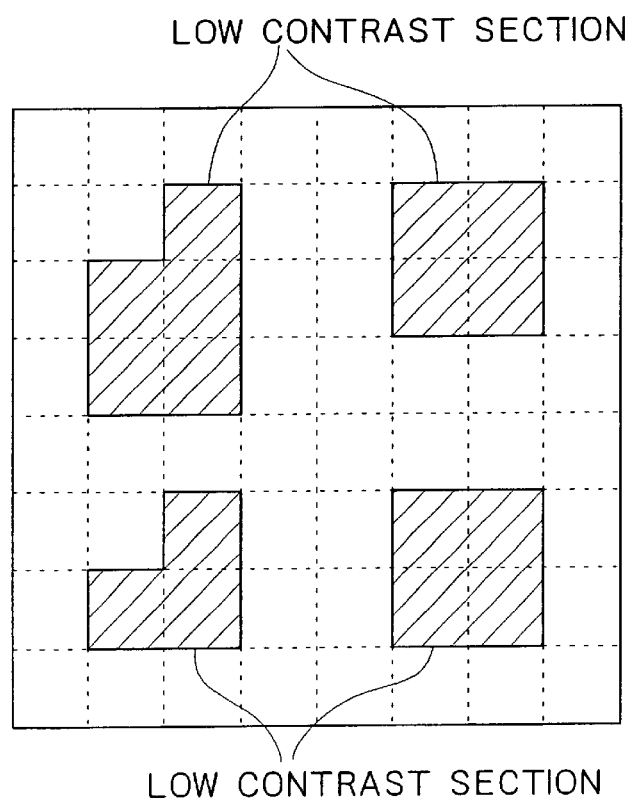
FIG. 15 is a diagram illustrating how to specify a low contrast region.

In step S5, as shown in FIG. 15, meshes in each of which the contrast is equal to or less than the specific threshold value are specified, and a low contrast section composed of these low contrast meshes is specified; and an area of the low contrast section is obtained. If a plurality of low contrast sections are present in the image, that is, a plurality of white mottles are present in the image, an average value of the areas of these low contrast sections is taken as an area of a low contrast section.

In step S6, black points in the image, in each of which a brightness level is lower than a specific threshold value, is detected irrespective of the meshes, and a length of a continuous line composed of the continuous black points is calculated. If a plurality of continuous lines are present in the image, the number of the continuous lines each having a length of a specific value or more, or the length of the longest continuous line may be obtained.

In step S7, an average grain size of crystals of the polysilicon film is judged on the basis of the contrast ratio, the area of the low contrast section composed of the continuous low contrast meshes, and the length of the continuous line.

Specifically, it can be discriminated whether grain sizes of crystals of the evaluated polysilicon film are small grain sizes, middle grain sizes (intermediate grain sizes), large grain sizes, or micro grain sizes by comparing the contrast ratio, the area of the low contrast section, and the length of the continuous line with specific thresholds (th1, th2, and th3), respectively, and making a decision on the basis of the following table.

TABLE 1

|  | small grain size | middle grain size | intermediate grain size | large grain size | micro grain size |
| --- | --- | --- | --- | --- | --- |
| contrast ratio (th1) | small | small | small | large | large |
| area of low contrast section (th2) | large | small | small | small | large |
| length of continuous line (th3) | small | small | small | small | large |
| AC value (th4) | small | large | small | small | small |

In addition, by using the AC value, it can be further discriminated whether grain sizes of crystals of the evaluated polysilicon film are middle grain sizes or intermediate grain sizes.

A second evaluation procedure for evaluating grain sizes of crystals of a polysilicon film will be described below.

Figure 16:
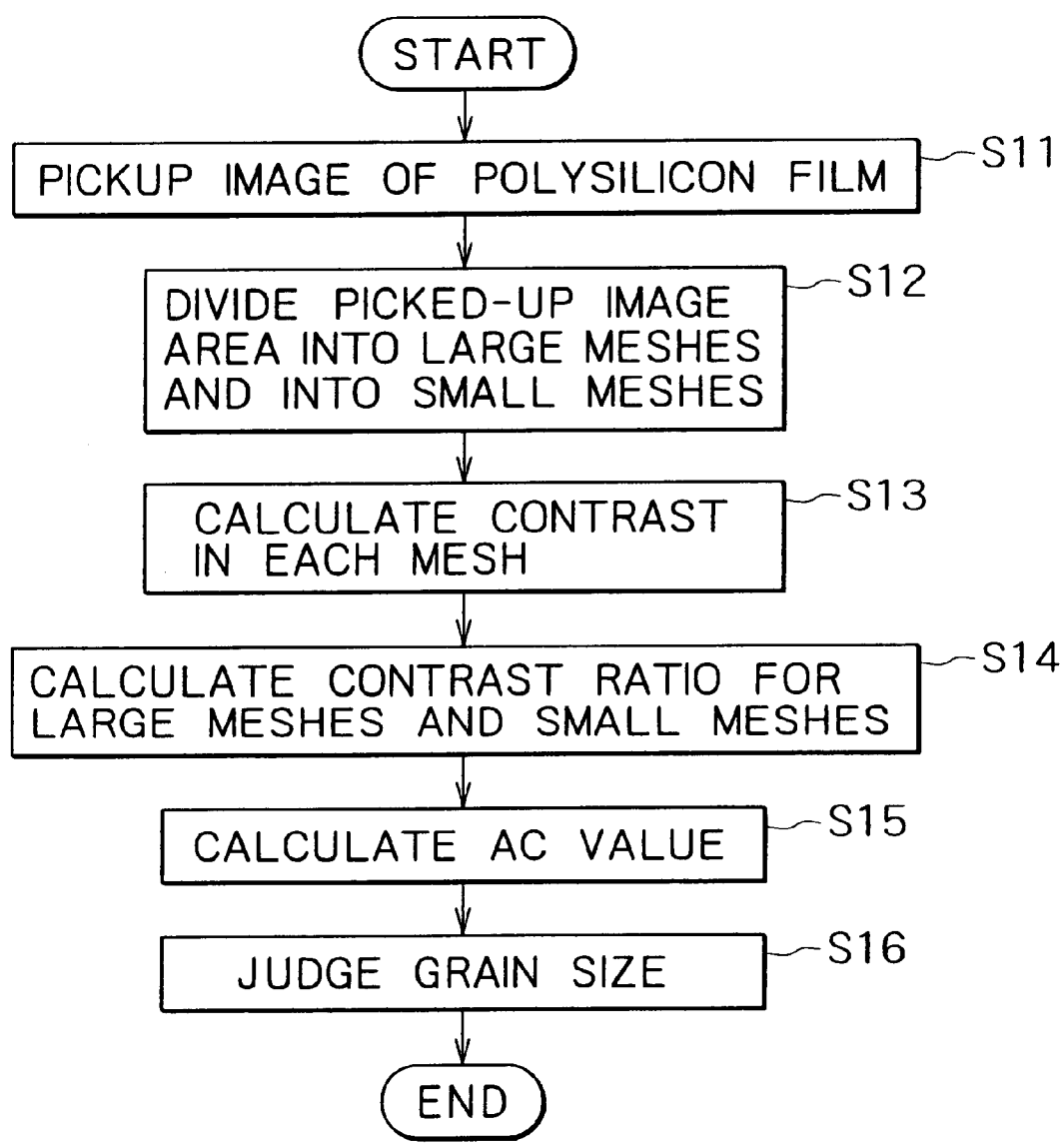
FIG. 16 is a flow chart showing a second evaluating procedure for evaluating grain sizes of crystals of a polysilicon film.

FIG. 16 is a flow chart illustrating the second evaluation procedure.

In step S11, a surface of a polysilicon film is picked-up. The picked-up image typically has a size of 11 $\mu$m×14 $\mu$m.

Figure 17:
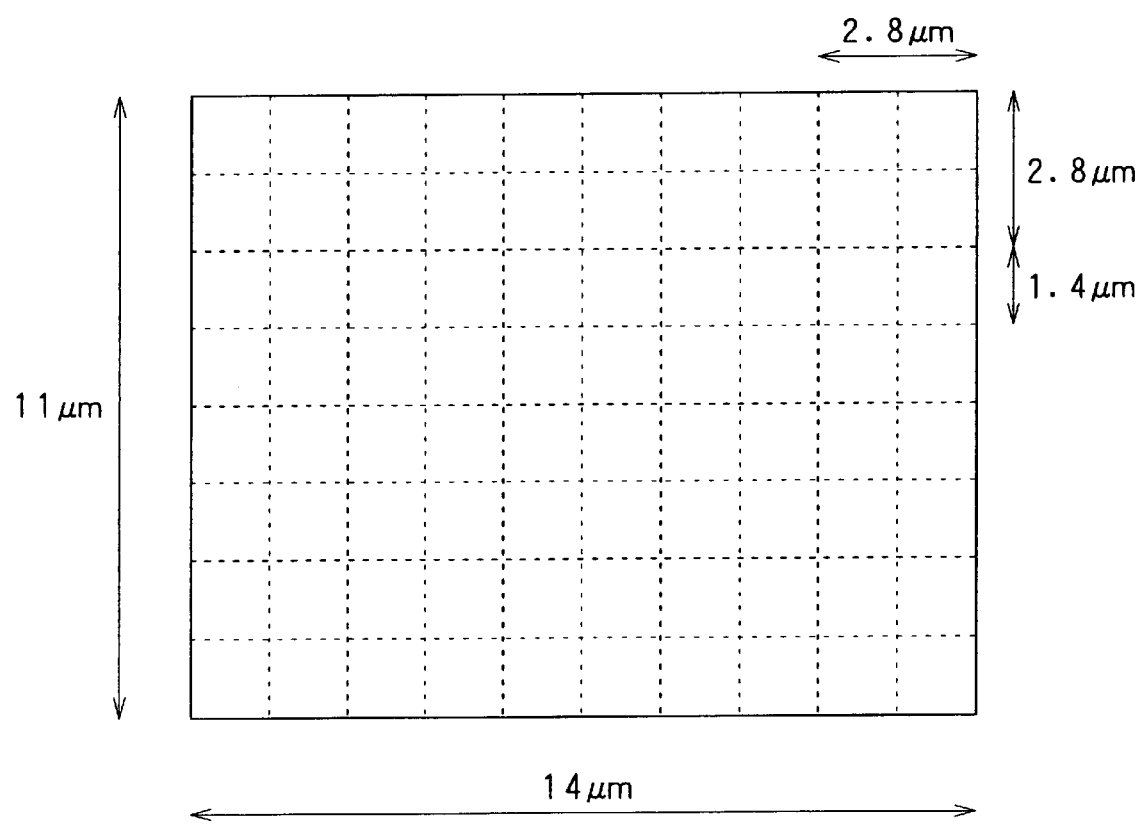
FIG. 17 is a diagram illustrating division of a picked-up image plane of a polysilicon film into large meshes and also division of the same picked-up image plane into small meshes.

In step S12, as shown in FIG. 17, the picked-up image is divided into large meshes and also the same picked-up image is divided into small meshes. The size of the small mesh has a size of 1.4 $\mu$m square, and the size of the large mesh has a size of 2.8 $\mu$m square. The size of the large mesh is preferably set to be sufficiently larger than that of a while mottle appearing for crystals of large grain sizes, for example, two or more times that of the white mottle. The size of the small mesh is preferably set to be sufficiently smaller than that of a white mottle appearing for crystals of large sizes, for example, one-half that of the white mottle.

In step S13, a contrast in each of the large meshes is calculated and a contrast in each of the small meshes is calculated. The contrast in each mesh is calculated by making use of a differential value of a brightness of an edge portion of the image, the degree of modulation of a brightness of each pixel, a standard deviation of respective pixels, and the like.

In step S14, a maximum contrast value and a minimum contrast value in the picked-up image, which are obtained for the large meshes, are extracted from the calculated contrast values, and the contrast ratio between the maximum and minimum contrast values is calculated, and similarly, a maximum contrast value and a minimum contrast value in the picked-up image, which are obtained for the small meshes, are extracted from the calculated contrast values, and the contrast ratio between the maximum and minimum contrast values is calculated.

In step S15, an AC value is calculated irrespective of the meshes.

In step S16, an average grain size of crystals of the polysilicon film is judged on the basis of the contrast ratio for the large meshes, the contrast ratio for the small meshes, and the AC value.

Specifically, it can be discriminated whether grain sizes of crystals of the evaluated polysilicon film are small grain sizes (intermediate grain sizes), middle grain sizes, large grain sizes, or micro grain sizes by comparing the contrast ratio for the large meshes, the contrast ratio for the small meshes, and the AC value, with specific thresholds respectively, and making a decision on the basis of the following table.

TABLE 2

|  | small grain size | middle grain size | intermediate grain size | large grain size | micro grain size |
| --- | --- | --- | --- | --- | --- |
| contrast ratio (for large meshes) | small | small | small | large | tolerably large |
| contrast ratio (for small meshes) | small | small | small | small | large |
| AC value | small | large | small | small | small |
| low contrast section | large | small | small | small | large |

Figure 18:
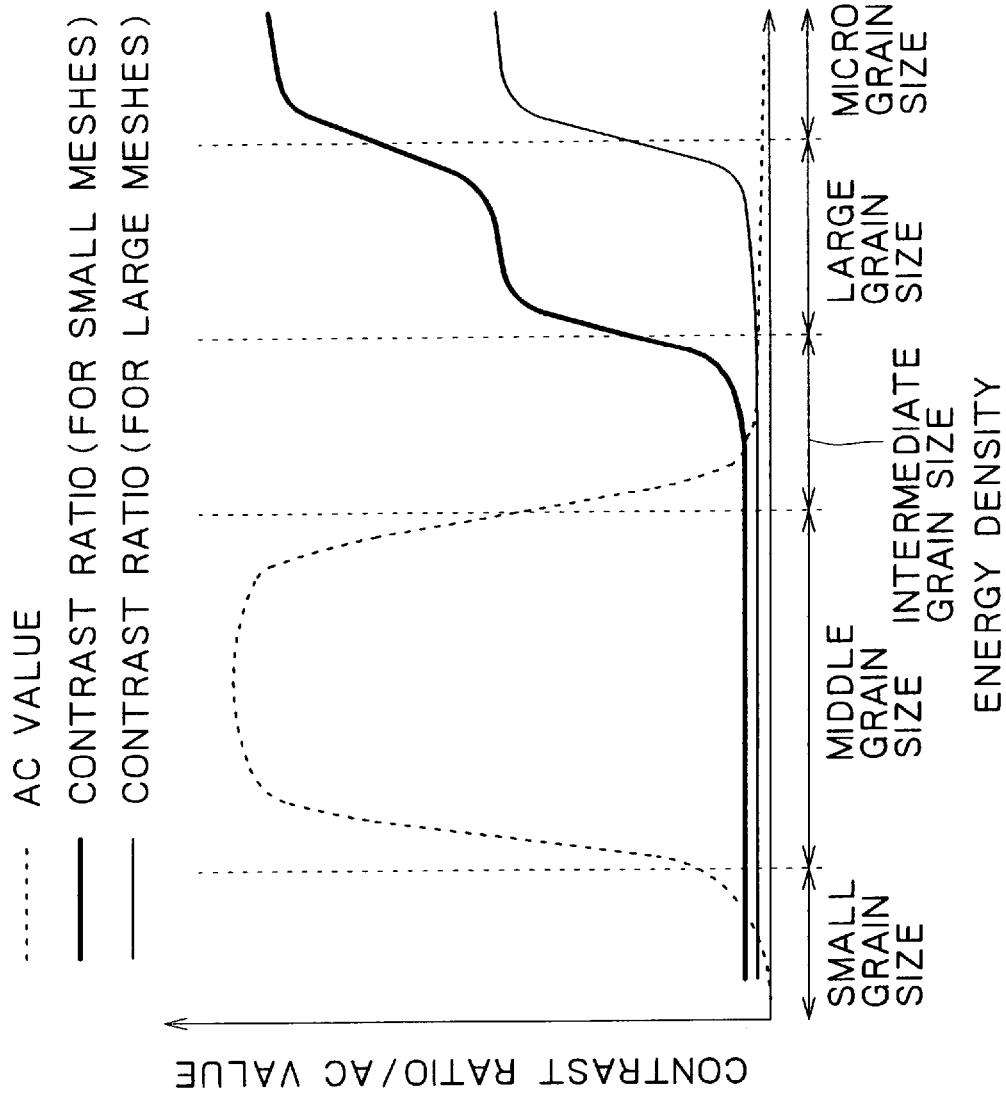
FIG. 18 is a graph showing a relationship between a change in energy density of a laser beam used for excimer laser annealing and a change in each of contrast ratio (for small meshes), contrast ratio (for large meshes), and AC value.

FIG. 18 is a graph showing a change in contrast ratio for the large meshes depending on an energy density, a change in contrast for the small meshes depending on the energy density, and a change in AC value depending on the energy density. As shown in the graph of FIG. 18, for crystals of large grain sizes or micro grain sizes, the contrast ratio for the small meshes is large, and for only crystals of micro grain sizes, the contrast ratio for the large meshes is large.

In addition, it can be discriminated whether grain sizes of crystals of a polysilicon film are small grain sizes or intermediate grain sizes on the basis of an area of a low contrast section for the small meshes.

A method of numerically evaluating linearity and periodicity of an image of a surface of a polysilicon film will be described below.

Figures 19A, 19B:
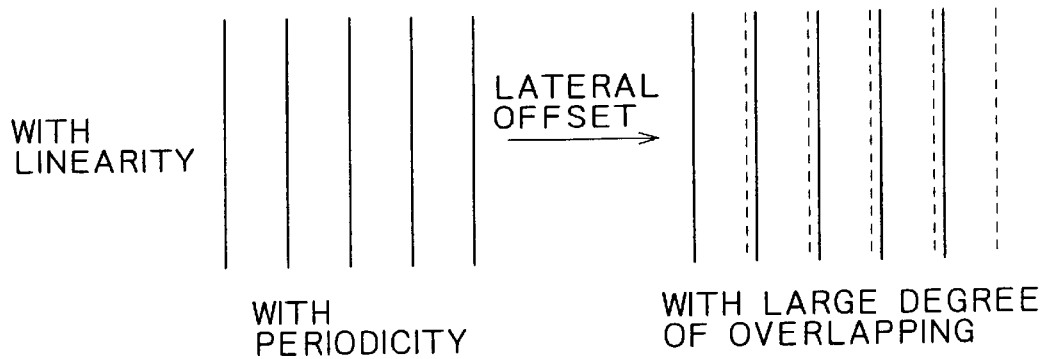
FIGS. 19A and 19B are diagrams schematically showing a picked-up image of a polysilicon film, which exhibits linearity and periodicity.
Figures 20A, 20B:
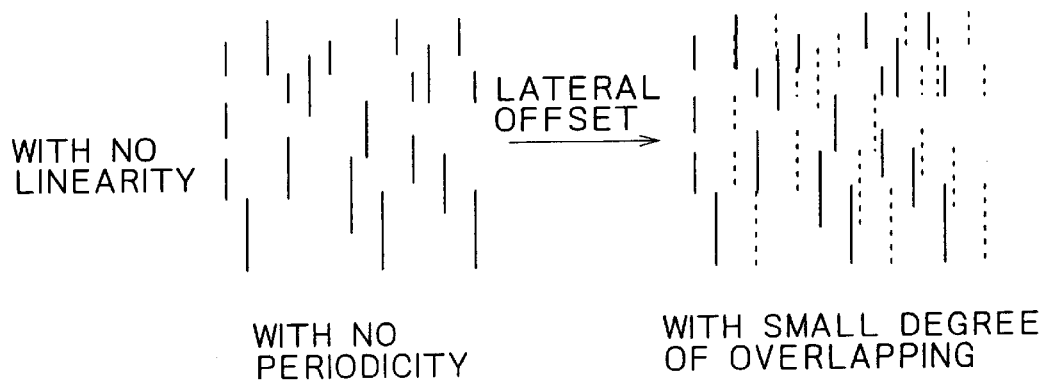
FIGS. 20A and 20B are diagrams schematically showing a picked-up image of a polysilicon film, which exhibits neither linearity nor periodicity.

A picked-up image of a polysilicon film having linearity and periodicity is typically shown in FIG. 19A, in which a number of straight lines are arrayed in parallel to each other with a gap between two of the straight lines kept constant. On the other hand, a picked-up image of a polysilicon film having neither linearity nor periodicity is typically shown in FIG. 20A, in which irregular short straight lines and the like irregularly appear. Numerical evaluation of linearity and periodicity of each of the images shown in FIGS. 19A and 20A may be performed by laterally offsetting the image in the direction perpendicular to a direction considered to have periodicity, and numerically evaluating a correlation between the original image and an offset image obtained by laterally offsetting the original image. For example, when the image having linearity and periodicity shown in FIG. 19A is laterally offset, as shown in FIG. 19B, a high correlation, that is, a large degree of overlapping between the original image and the offset image appears with a certain cycle, that is, for a specific lateral offset amount. On the other hand, even when the image having neither linearity nor periodicity shown in FIG. 20A is laterally offset, as shown in FIG. 20B, a high correlation, that is, a large degree of overlapping between the original image and the offset image does not appear with a certain cycle.

Periodicity of a picked-up image of a surface of a polysilicon film can be numerically evaluated by laterally offsetting the image, and numerically expressing a correlation between the original image and the offset image. As one method of realizing the above numerical evaluation manner, there is known a method of calculating an autocorrelation function of an image, calculating a peak value and a side-peak value of the autocorrelation function, and obtaining a ratio between the peak value and the side-peak value. The peak value means a value obtained by subtracting the second minimum value (which is used for reducing a defocus value, and may be the first minimum value or any of the second and later minimum values) in a y-direction based on an origin from the origin. The side-peak value means a value obtained by subtracting the second minimum value in the y-direction based on the origin from the second maximum value (not containing the origin) in the y-direction from the origin.

It is to be noted that states of crystals of a polysilicon film can be judged by evaluating either of linearity and periodicity of an image of a surface of the polysilicon film.

As other methods of numerically evaluating a picked-up image of a surface of a polysilicon film having linearity and/or periodicity, there are known a method of adding all pixel values of a standardized image in a direction having linearity and calculating the degree of a modulation thereof; a method of subjecting a standardized image to two-dimensional Fourier transform, and taking an intensity of a certain frequency component from the transformed image; a method of extracting a coordinate of an extreme value (a minimum value or a maximum value) of an image (considered to have linearity in a y-direction), and taking a dispersion in an x-direction of coordinates in a range elongated in the y-direction (a center in the x-direction is taken as an average value of extreme value×coordinate, and a length in the x-direction is taken as an arrangement pitch in the x-direction); and a method of extracting a coordinate of an extreme value (a minimum value or a maximum value) in an image considered to have linearity in a y-direction, and taking an angle between portions near upper and lower sides of a coordinate of a range elongated in the y-direction (a center in the x-direction is taken as an average value of extreme value×coordinate, and a length in the x-direction is taken as an arrangement pitch in the x-direction).

A procedure for evaluating states of crystals of a polysilicon film will be described below. The image processing computer 29 evaluates states of crystals of a polysilicon film by calculating a value (hereinafter, referred to as "AC value"), which numerically expresses periodicity of a picked-up image of a surface of the polysilicon film by using autocorrelation of the image, and evaluating linearity and periodicity of a surface spatial structure of the polysilicon film on the basis of the AC value.

Figure 21:
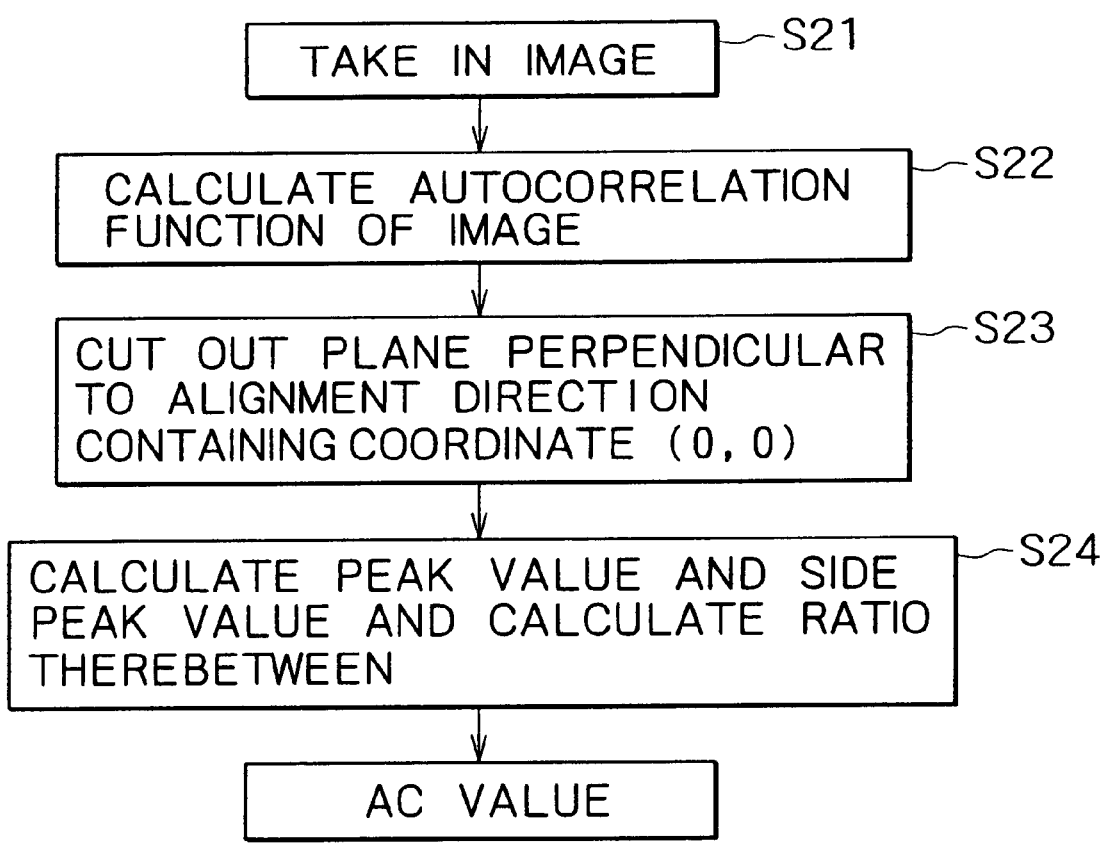
FIG. 21 is a flow chart illustrating a flow chart illustrating an evaluating procedure for evaluating a polysilicon film, a picked-up image of which exhibits linearity and periodicity.

The procedure processing the evaluation is performed in accordance with a flow chart shown in FIG. 21. In step S21, an image of a surface of a polysilicon film is taken in the image processing computer 29. In step S22, an autocorrelation function of the taken-in image is calculated. In step S23, a plane perpendicular to an alignment direction, which plane contains a coordinate (0,0) of the image, is cut out of the image. In step S24, a peak value and a side-peak value of the autocorrelation function on the plane cut out in step S23 are calculated, and the AC value is obtained as a ratio between the peak value and the side-peak value.

Here, the autocorrelation function can be expressed as follows:

$$R(\tau) = \lim_{T\to\infty} \frac{1}{T} \int_0^T f(x)f(x+\tau)dx$$

The autocorrelation function R ($\tau$) indicates a correlation between a function f(x) and a function obtained by translating the function f(x) in an x-direction by a value $\tau$.

The polysilicon film evaluating system 20 obtains an autocorrelation function of a surface image of a polysilicon film by using the following Wiener-Khinchin theorem. It is to be noted that in the calculation using the Wiener-Khinchin theorem, information on the concretely taken-in image is designated by character "i".

Step 1: the taken-in image "i" is subjected to two-dimensional Fourier transform (f=fourier (i)).

Step 2: the Fourier transform "f" is squared, to create a power spectrum "ps" (ps=|f|$^2$)

Step 3: the power spectrum "ps" is subjected to inverse Fourier transform, to create a two-dimensional autocorrelation function "ac" (ac=inversefourier (ps)).

Step 4: an absolute value of the autocorrelation function "ac" is taken as a real value of the autocorrelation function (aca=|ac|)

Figure 22:
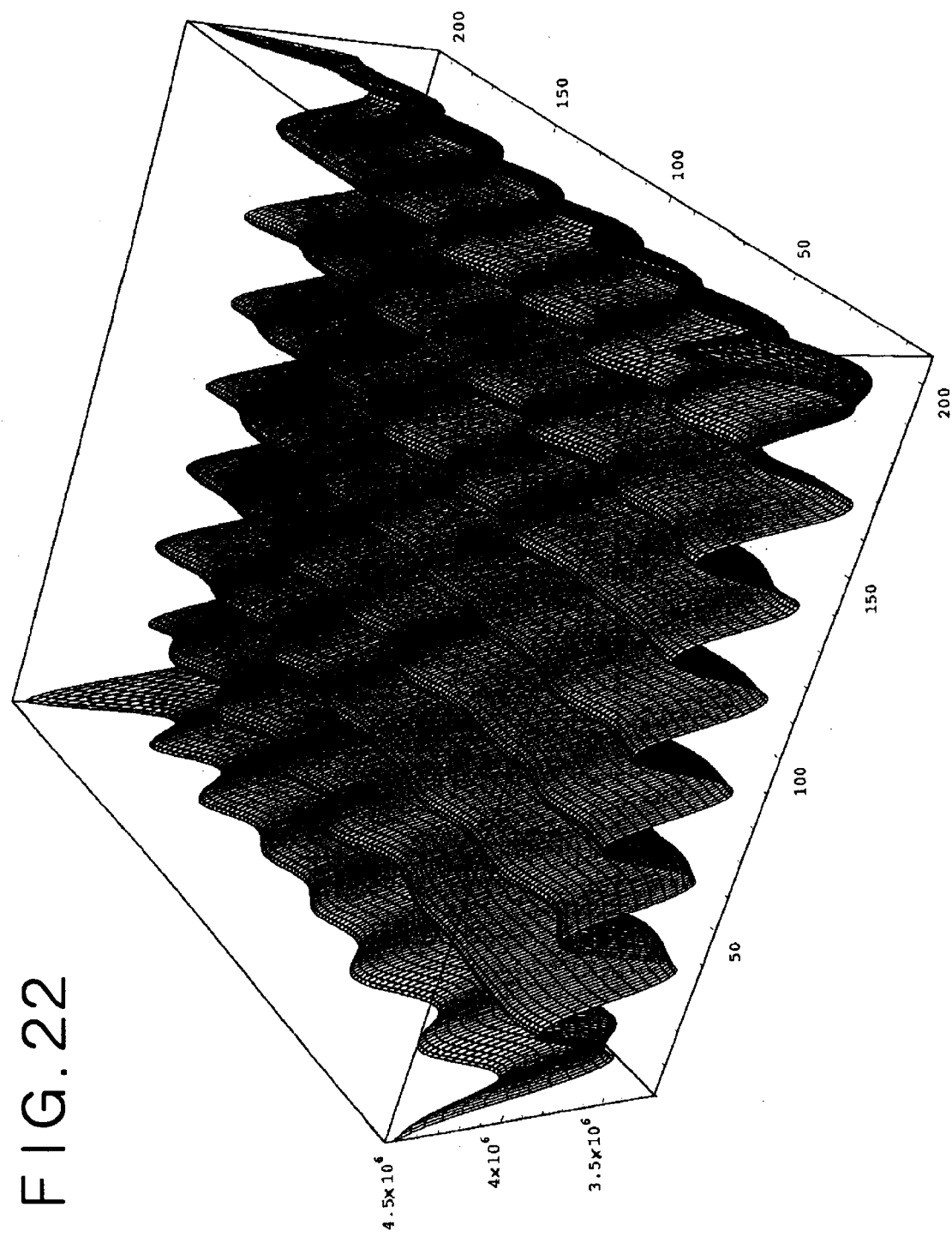
FIG. 22 is a diagram illustrating an autocorrelation function of an image with a high periodicity.
Figure 23:
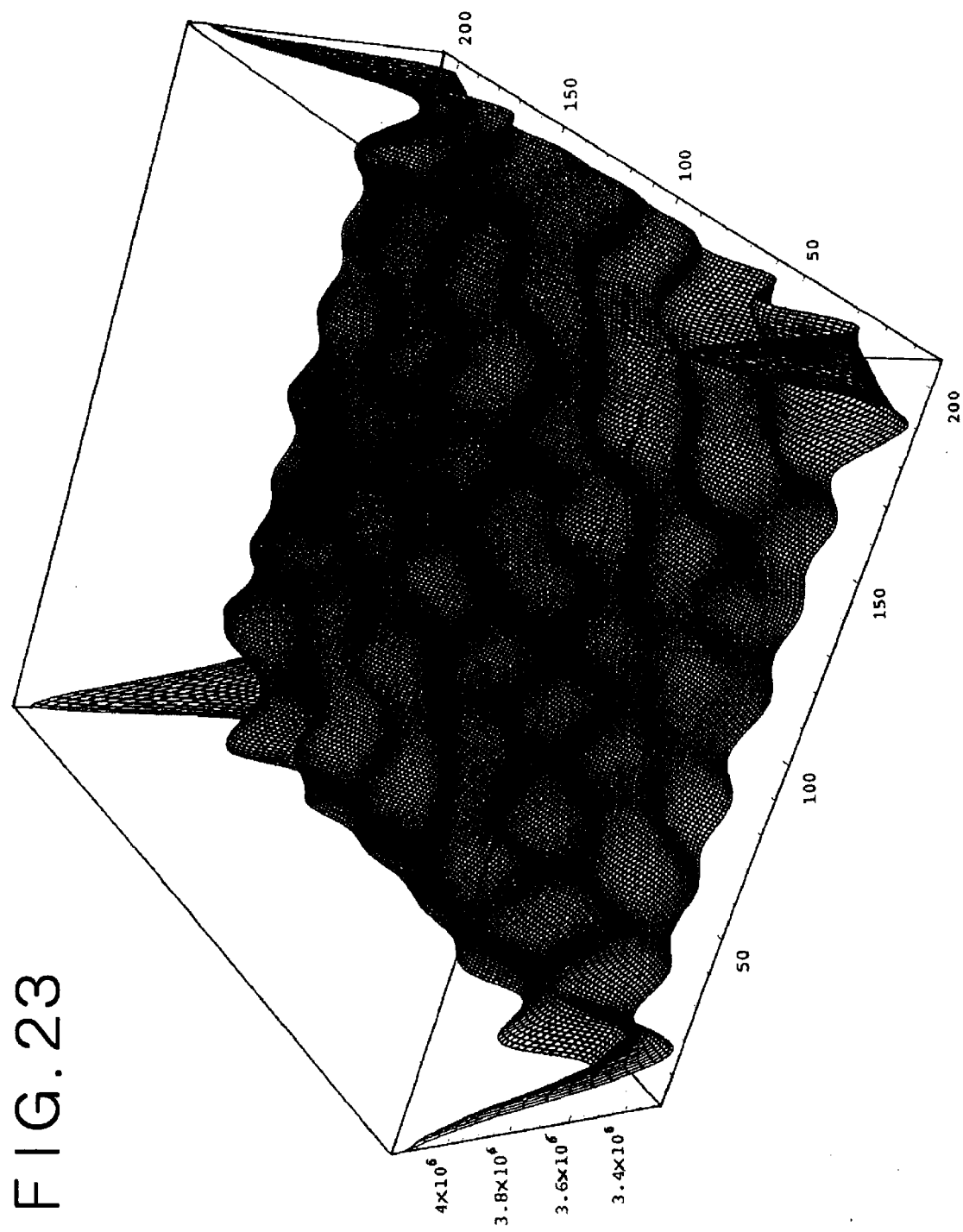
FIG. 23 is a diagram illustrating an autocorrelation function of an image with a low periodicity.

The autocorrelation function "aca" thus created is expressed as shown in each of FIGS. 22 and 23. FIG. 22 shows an image whose autocorrelation is high, that is, an autocorrelation function of a surface spatial structure of a polysilicon film having good linearity and periodicity. FIG. 23 shows an image whose autocorrelation is low, that is, an autocorrelation function of a surface spatial structure of a polysilicon film having poor linearity and periodicity.

The polysilicon film evaluating system 20 further cuts a plane, which is perpendicular to an alignment direction (that is, a direction having linearity) and contains a coordinate (0,0) of the image, out of the autocorrelation image thus calculated by using the Wiener-Khinchin theorem, and obtains a function on the plane thus cut out of the autocorrelation image. The reason why the plane containing the coordinate (0, 0) is cut is to standardize the autocorrelation function which is changed depending on experimental parameters such as illumination light quantity, CCD gain, and the like.

The function thus obtained on the plane cut out of the autocorrelation image corresponds to the autocorrelation function R ($\tau$) in the direction perpendicular to the above-described alignment direction.

Figure 24:
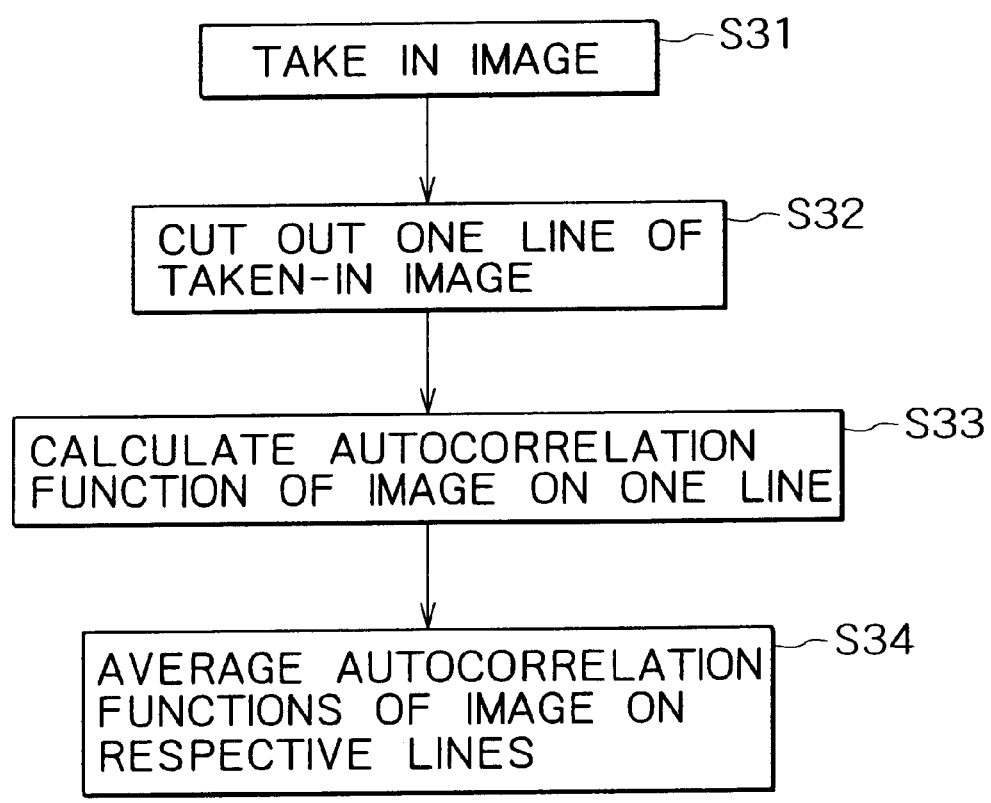
FIG. 24 is a flow chart illustrating another evaluation procedure for evaluating an image of a polysilicon film, a picked-up image of which exhibits linearity and periodicity.

It is to be noted that the above-described steps S21 to 23 may be replaced with steps S31 to 34 shown in FIG. 24.

The evaluation processing procedure shown in the flow chart of FIG. 24 will be described below. In step S31, an image of a surface of a polysilicon film is taken in the image processing computer 29. In step S32, one line of the taken-in image in the direction (y-direction having periodicity) perpendicular to a laser beam traveling direction (x-direction having linearity) is cut out of the image. In step S33, an autocorrelation function of the one line of the image is calculated. In step S34, these operations are repeated by several times, to average the autocorrelation functions of respective lines of the image, as needed.

The autocorrelation function in this case can be calculated by using the Wiener-Khinchin theorem as follows. It is to be noted that in the following calculation, information on the one line of the concretely taken-in image is designated by character "I".

Step 1: the one line "I" of the taken-in image is subjected to Fourier transform (fI=fourier (I)).

Step 2: the Fourier transform "fI" is squared, to create a power spectrum "psI" (psI=|fI|$^2$)

Step 3: the power spectrum "psI" is subjected to inverse Fourier transform, to create a two-dimensional autocorrelation function "acI" (acI=inversefourier (psI)).

Step 4: an absolute value of the autocorrelation function "acI" is taken as a real value "acaI" of the autocorrelation function (acaI=|acI|).

Figure 25:
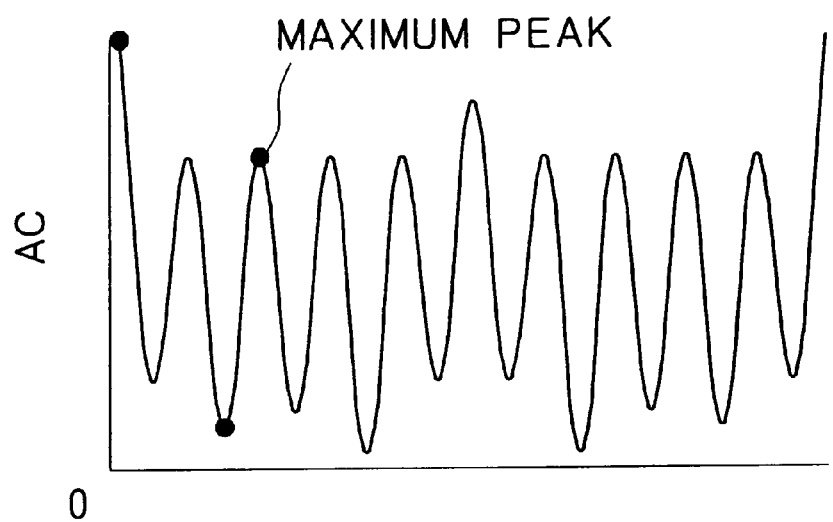
FIG. 25 is a graph illustrating an autocorrelation function of an image with a high periodicity as a result of evaluation performed by the evaluating procedure shown in FIG. 24.
Figure 26:
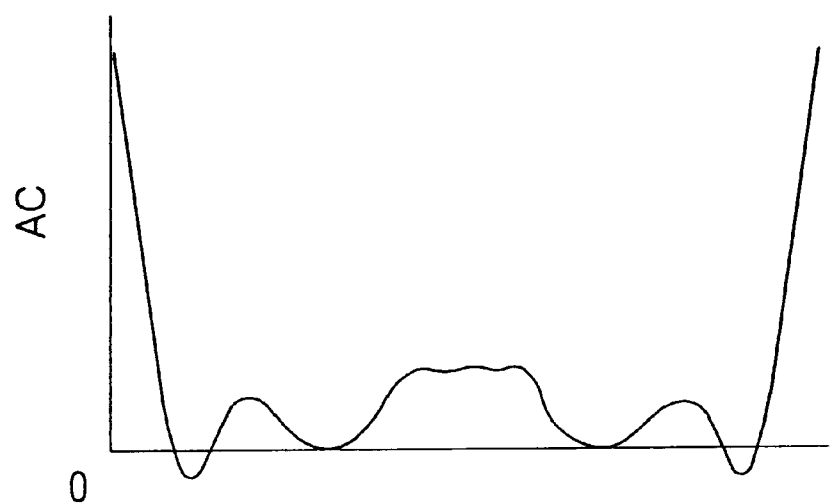
FIG. 26 is a graph illustrating an autocorrelation function of an image with a low periodicity as a result of evaluation performed by the evaluating procedure shown in FIG. 24.

The autocorrelation function "acaI" thus created is expressed as shown in each of FIGS. 25 and 26. FIG. 25 shows an image whose autocorrelation is high, that is, an autocorrelation function of a surface spatial structure of a polysilicon film having good linearity and periodicity. FIG. 26 shows an image whose autocorrelation is low, that is, an autocorrelation function of a surface spatial structure of a polysilicon film having poor linearity and periodicity.

The calculation of the autocorrelation function of the above one line of the picked-up image is repeated for all lines of the picked-up image, to average the autocorrelation functions of all of the lines of the picked-up image. The average autocorrelation function corresponds to an autocorrelation function R ($\tau$) in the direction perpendicular to the above-described alignment direction (direction having linearity).

The polysilicon film evaluating system 20 takes a maximum peak value and a side-peak value from the function thus obtained and calculates a ratio between the maximum peak value to the side-peak value. Such a ratio is taken as the AC value.

Accordingly, for an image having a high autocorrelation, that is, for an image in which linearity and periodicity of a surface spatial structure of a polysilicon film are desirable, since a difference between the maximum peak value and the side-peak value is large, the AC value becomes large. On the other hand, for an image having a low autocorrelation, that is for an image in which linearity and periodicity of a surface spatial structure of a polysilicon film are undesirable, since a difference between the maximum peak value and the side-peak value is small, the AC value becomes small.

As described above, in the top-gate type TFT according to the present invention, a surface image of a polysilicon film is picked-up and an autocorrelation function of the picked-up image is calculated, and linearity and periodicity of a surface spatial structure of the polysilicon film are numerically evaluated.

While the preferred embodiments of the present invention have been described using specific terms, such description is for illustrative purposes only, and it is to be understood that changes and variations may be made without departing from the spirit or scope of the following claims.

What is claimed is:

1. A polysilicon evaluating method of evaluating a polysilicon film formed by annealing an amorphous silicon film, comprising the steps of:

picking up an image of a surface of the polysilicon film;

dividing the picked-up image into a plurality of regions and calculating a contrast in each of the regions divided from the picked-up image;

detecting a high contrast region and a low contrast region and comparing the contrasts in the high contrast and low contrast regions with each other; and evaluating a state of the polysilicon film on the basis of the comparison result.

2. A polysilicon evaluating method according to claim 1, wherein a contrast ratio between the contrast in the low contrast region and the contrast in the high contrast region is calculated; and the state of the polysilicon film is evaluated on the basis of the contrast ratio.

3. A polysilicon evaluating method according to claim 1, wherein a polysilicon film, which is formed by subjecting an amorphous silicon film to laser annealing, is evaluated.

4. A polysilicon evaluating method according to claim 3, wherein a polysilicon film, which is formed by subjecting an amorphous silicon film to laser annealing using a linear laser beam with which a linear portion of the amorphous silicon film is irradiated, is evaluated.

5. A polysilicon evaluating method according to claim 4, wherein a polysilicon film, which is formed by subjecting an amorphous silicon film to excimer laser annealing, is evaluated.

6. A polysilicon evaluating system for evaluating a polysilicon film formed by annealing an amorphous silicon film, comprising:

pick-up means of picking up an image of a surface of the polysilicon film; and evaluation means of dividing the picked-up image into a plurality of regions, calculating a contrast in each of the regions divided from the picked-up image, detecting a high contrast region and a low contrast region, comparing the contrasts in the high contrast and low contrast regions with each other, and evaluating the state of the polysilicon film on the basis of the comparison result.

7. A polysilicon evaluating system according to claim 6, wherein said evaluation means calculates a contrast ratio between the contrast in the low contrast region and the contrast in the high contrast region, and evaluates the state of the polysilicon film on the basis of the contrast ratio.

8. A polysilicon evaluating system according to claim 6, wherein a polysilicon film, which is formed by subjecting an amorphous silicon film to laser annealing is evaluated.

9. A polysilicon evaluating system according to claim 8, wherein a polysilicon film, which is formed by subjecting an amorphous silicon film to laser annealing using a linear laser beam with which a linear portion of the amorphous silicon film is irradiated, is evaluated.

10. A polysilicon evaluating system according to claim 9, wherein a polysilicon film, which is formed by subjecting an amorphous silicon film to excimer laser annealing, is evaluated.

11. A thin film transistor fabricating method of fabricating a thin film transistor, comprising:

amorphous silicon forming step of forming an amorphous silicon film;

polysilicon film forming step of forming a polysilicon film by annealing the amorphous silicon film; and evaluating step of picking up an image of a surface of the polysilicon film, dividing the picked-up image into a plurality of regions, calculating a contrast in each of the regions divided from the picked-up image, detecting a high contrast region and a low contrast region, comparing the contrasts in the high contrast and low contrast regions, and evaluating the state of the polysilicon film on the basis of the comparison result.

12. A thin film transistor fabricating method according to claim 11, wherein in said evaluating step, a contrast ratio between the contrast in the low contrast region and the contrast in the high contrast region is calculated, and the state of the polysilicon film is evaluated on the basis of the contrast ratio.

13. A thin film transistor fabricating method according to claim 11, wherein in said polysilicon film forming step, the amorphous silicon film is subjected to laser annealing.

14. A thin film transistor fabricating method according to claim 13, wherein in said polysilicon film forming step, an amorphous silicon film is subjected to laser annealing using a linear laser beam with which a linear portion of the amorphous silicon film is irradiated.

15. A thin film transistor fabricating method according to claim 14, wherein in said polysilicon film forming step, an amorphous silicon film is subjected to excimer laser annealing.

16. A thin film transistor fabricating method according to claim 15, wherein in said evaluating step, an energy density of an excimer laser used for excimer laser annealing, which is given in said polysilicon film forming step, is controlled on the basis of the evaluated state of the polysilicon film.

17. A thin film transistor fabricating method according to claim 16, wherein in said evaluating step, the energy density of a laser beam used for excimer laser annealing is controlled such that a contrast ratio between the contrast in a low contrast region and the contrast in a high contrast region is higher than a specific value, and an area of a portion composed of continuous contrast low regions is smaller than a specific value.

18. A thin film transistor fabricating system for fabricating a thin film transistor, comprising:

an amorphous silicon forming device for forming an amorphous silicon film;

a polysilicon film forming device for forming a polysilicon film by annealing the amorphous silicon film; and an evaluating device for picking up an image of a surface of the polysilicon film, dividing the picked-up image into a plurality of regions, calculating a contrast in each of the regions divided from the picked-up image, detecting a high contrast region and a low contrast region, comparing the contrasts in the high contrast and low contrast regions, and evaluating the state of the polysilicon film on the basis of the comparison result.

19. A thin film transistor fabricating system according to claim 18, wherein said evaluating device calculates a contrast ratio between the contrast in the low contrast region and the contrast in the high contrast region, and evaluates the state of the polysilicon film on the basis of the contrast ratio.

20. A thin film transistor fabricating system according to claim 18, wherein in said polysilicon film forming device, the amorphous silicon film is subjected to laser annealing.

21. A thin film transistor fabricating system according to claim 20, wherein in said polysilicon film forming device, an amorphous silicon film is subjected to laser annealing using a linear laser beam with which a linear portion of the amorphous silicon film is irradiated.

22. A thin film transistor fabricating system according to claim 21, wherein in said polysilicon film forming device, an amorphous silicon film is subjected to excimer laser annealing.

23. A thin film transistor fabricating system according to claim 22, wherein in said evaluating device, an energy density of an excimer laser used for excimer laser annealing, which is given by said polysilicon film forming device, is controlled on the basis of the evaluated state of the polysilicon film.

24. A thin film transistor fabricating system according to claim 23, wherein in said evaluating device, the energy density of a laser beam used for excimer laser annealing is controlled such that a contrast ratio between the contrast in a low contrast region and the contrast in a high contrast region is higher than a specific value, and an area of a portion composed of continuous contrast low regions is smaller than a specific value.

* * * * *

UNITED STATES PATENT AND TRADEMARK OFFICE
CERTIFICATE OF CORRECTION

PATENT NO. : 6,673,639 B2
DATED : January 6, 2004
INVENTOR(S) : Hiroyuki Wada et al.

It is certified that error appears in the above-identified patent and that said Letters Patent is hereby corrected as shown below:

Column 12,
Line 47, change "while" to -- white --.

Column 16,
Line 9, change "(psI=|f|$^2$)" to -- (psI+|f I|$^2$) --.

Signed and Sealed this

Twenty-second Day of June, 2004

JON W. DUDAS
*Acting Director of the United States Patent and Trademark Office*